United States Patent
Mondry et al.

(10) Patent No.: US 9,498,292 B2
(45) Date of Patent: Nov. 22, 2016

(54) SINGLE SITE ROBOTIC DEVICE AND RELATED SYSTEMS AND METHODS

(71) Applicant: Board of Regents of the University of Nebraska, Lincoln, NE (US)

(72) Inventors: Jack Mondry, Stillwater, MN (US); Shane Farritor, Lincoln, NE (US); Eric Markvicka, Ravenna, NE (US); Thomas Frederick, Omaha, NE (US); Joseph Bartels, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 7 days.

(21) Appl. No.: 13/839,422

(22) Filed: Mar. 15, 2013

(65) Prior Publication Data
US 2014/0039515 A1 Feb. 6, 2014

Related U.S. Application Data

(60) Provisional application No. 61/640,879, filed on May 1, 2012.

(51) Int. Cl.
*A61B 19/00* (2006.01)
*B25J 9/00* (2006.01)
*A61B 17/29* (2006.01)

(52) U.S. Cl.
CPC .......... *A61B 19/2203* (2013.01); *A61B 34/30* (2016.02); *B25J 9/0084* (2013.01); *A61B 90/361* (2016.02); *A61B 2017/2906* (2013.01); *A61B 2034/2048* (2016.02); *A61B 2034/2051* (2016.02); *A61B 2034/302* (2016.02)

(58) Field of Classification Search
CPC .......... A61B 19/2203; A61B 19/5212; A61B 2019/2215; A61B 2019/5248; A61B 2019/5251; A61B 2017/2906
USPC ..................... 606/1, 53, 108, 130, 138, 139; 700/245–263
See application file for complete search history.

(56) References Cited

U.S. PATENT DOCUMENTS

| | | | |
|---|---|---|---|
| 3,870,264 A | 3/1975 | Robinson | |
| 3,989,952 A | 11/1976 | Hohmann | |

(Continued)

FOREIGN PATENT DOCUMENTS

| | | |
|---|---|---|
| EP | 2286756 | 2/2011 |
| EP | 2286756 A1 | 2/2011 |

(Continued)

OTHER PUBLICATIONS

Xu et al., "System Design of an Insertable Robotic Effector Platform for Single Access (SPA) Surgery", The 2009 IEEE/RSJ International Conference on Intelligent Robots and Systems, Oct. 11-15, 2009, St Louis MO USA pp. 5546-5552.*

(Continued)

*Primary Examiner* — Gary Jackson
*Assistant Examiner* — Boniface N Nganga
(74) *Attorney, Agent, or Firm* — Davis, Brown, Koehn, Shors & Roberts, P.C.

(57) ABSTRACT

The embodiments disclosed herein relate to various medical device components, including components that can be incorporated into robotic and/or in vivo medical devices. Certain embodiments include various medical devices for in vivo medical procedures.

20 Claims, 36 Drawing Sheets

(56) References Cited

U.S. PATENT DOCUMENTS

| | | |
|---|---|---|
| 4,246,661 A | 1/1981 | Pinson |
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyaki |
| 4,623,183 A | 11/1986 | Amori |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,897,014 A | 1/1990 | Tietze |
| 4,922,755 A | 5/1990 | Oshiro et al. |
| 4,990,050 A | 2/1991 | Tsuge et al. |
| 5,019,968 A | 5/1991 | Wang et al. |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,388,528 A | 2/1995 | Pelrine et al. |
| 5,436,542 A | 7/1995 | Petelin et al. |
| 5,441,494 A | 8/1995 | Ortiz |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Okamoto et al. |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Tierney et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |

(56) References Cited

U.S. PATENT DOCUMENTS

| | | |
|---|---|---|
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,678,043 B2 | 3/2010 | Gilad |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,179,073 B2 | 5/2012 | Farritor et al. |
| 8,353,897 B2 | 1/2013 | Doyle et al. |
| 8,604,742 B2 | 12/2013 | Farritor et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |

(56) References Cited

U.S. PATENT DOCUMENTS

| | | |
|---|---|---|
| 2002/0026186 A1 | 2/2002 | Woloszko et al. |
| 2002/0038077 A1 | 3/2002 | de la Torre et al. |
| 2002/0065507 A1 | 5/2002 | Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 7/2008 | Rioux et al. |
| 2008/0164079 A1 | 7/2008 | Jacobsen |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1* | 2/2009 | Farritor et al. ............... 606/130 |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1* | 7/2009 | Farritor et al. ............... 606/130 |
| 2009/0234369 A1 | 9/2009 | Bax et al. |
| 2009/0236400 A1 | 9/2009 | Cole et al. |
| 2009/0240246 A1 | 9/2009 | Deville et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Scott |
| 2010/0204713 A1 | 8/2010 | Ruiz |
| 2010/0245549 A1 | 9/2010 | Allen et al. |
| 2010/0262162 A1 | 10/2010 | Omori |
| 2010/0292691 A1 | 11/2010 | Brogna |
| 2010/0318059 A1 | 12/2010 | Farritor et al. |
| 2011/0015569 A1 | 1/2011 | Kirschenman et al. |
| 2011/0020779 A1* | 1/2011 | Hannaford et al. .......... 434/262 |
| 2011/0071347 A1 | 3/2011 | Rogers et al. |
| 2011/0071544 A1 | 3/2011 | Steger et al. |
| 2011/0077478 A1 | 3/2011 | Freeman et al. |
| 2011/0082365 A1 | 4/2011 | McGrogan et al. |
| 2011/0152615 A1* | 6/2011 | Schostek et al. ............ 600/111 |
| 2011/0224605 A1 | 9/2011 | Farritor et al. |
| 2011/0230894 A1* | 9/2011 | Simaan et al. ............... 606/130 |
| 2011/0237890 A1 | 9/2011 | Farritor et al. |

(56) References Cited

U.S. PATENT DOCUMENTS

| | | | |
|---|---|---|---|
| 2011/0238080 A1* | 9/2011 | Ranjit et al. | 606/130 |
| 2011/0270443 A1* | 11/2011 | Kamiya et al. | 700/245 |
| 2012/0035582 A1 | 2/2012 | Nelson et al. | |
| 2012/0109150 A1* | 5/2012 | Quaid et al. | 606/130 |
| 2012/0253515 A1* | 10/2012 | Coste-Maniere et al. | 700/250 |
| 2013/0041360 A1 | 2/2013 | Farritor | |
| 2013/0131695 A1* | 5/2013 | Scarfogliero et al. | 606/130 |

FOREIGN PATENT DOCUMENTS

| | | | |
|---|---|---|---|
| EP | 2329787 | 8/2011 | |
| JP | 2004144533 | 5/1990 | |
| JP | 5115425 | 5/1993 | |
| JP | 07 136173 | 5/1995 | |
| JP | 7306155 | 11/1995 | |
| JP | 08-224248 | 9/1996 | |
| JP | 2001505810 | 5/2001 | |
| JP | 2004322310 | 6/2004 | |
| JP | 2004180781 | 7/2004 | |
| JP | 2004329292 | 11/2004 | |
| KR | WO 2010050771 A2 * | 5/2010 | A61B 19/2203 |
| WO | WO 92/21291 | 12/1992 | |
| WO | WO 02/082979 | 10/2002 | |
| WO | WO 02/100256 | 12/2002 | |
| WO | WO 2005/009211 | 2/2005 | |
| WO | WO 2005009211 | 2/2005 | |
| WO | WO 2006 005075 | 1/2006 | |
| WO | WO 2006/079108 | 1/2006 | |
| WO | WO 2006/052927 | 5/2006 | |
| WO | WO2006079108 | 7/2006 | |
| WO | WO 2007/111571 | 10/2007 | |
| WO | WO 2007/149559 | 12/2007 | |
| WO | WO 2009023851 A1 | 2/2009 | |
| WO | WO 2009/144729 | 12/2009 | |
| WO | WO2010/042611 | 4/2010 | |
| WO | WO2010/046823 | 4/2010 | |
| WO | WO 2011/118646 A1 | 3/2011 | |
| WO | WO 2011/135503 A1 | 11/2011 | |
| WO | WO 2013009887 | 1/2013 | |

OTHER PUBLICATIONS

Patronik et al., "Development of a Tethered Epicardial Crawler for Minimally Invasive Cardiac Therapies," IEEE, pp. 239-240.

Patronik et al., "Crawling on the Heart: A Mobile Robotic Device for Minimally Invasive Cardiac Interventions," MICCAI, 2004, pp. 9-16.

Patronik et al., "Preliminary evaluation of a mobile robotic device for navigation and intervention on the beating heart," Computer Aided Surgery, 10(4): 225-232, Jul. 2005.

Peirs et al., "A miniature manipulator for integration in a self-propelling endoscope," Sensors and Actuators A, 2001, 92: 343-349.

Peters, "Minimally Invasive Colectomy: Are the Potential Benefits Realized?" Dis Colon Rectum 1993; 36: 751-756.

Phee et al., "Analysis and Development of Locomotion Devices for the Gastrointestinal Tract," IEEE Transaction on Biomedical Engineering, vol. 49, No. 6, Jun. 2002, pp. 613-616.

Phee et al., "Development of Microrobotic Devices for Locomotion in the Human Gastrointestinal Tract," International Conference on Computational Intelligence, Robotics and Autonomous Systems (CIRAS 2001), Nov. 28-30, 2001, Singapore.

Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, I pg.

Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006e.

Rentschler et al., Mobile In Vivo Biopsy Robot, IEEE International Conference on Robotics and Automation, Orlando, Florida, May 2006, pp. 4155-4160.

Rentschler et al., "Miniature in vivo Robots for Remote and Harsh Environments," IEEE Transactions on Information Technology in Biomedicine, Jan. 2006; 12(1): 66-75.

Rentschler et al., "An In Vivo Mobile Robot for Surgical Vision and Task Assistance," Journal of Medical Devices, Mar. 2007, vol. 1: 23-29.

Rentschler et al., "In vivo Mobile Surgical Robotic Task Assistance," 1 pg.

Rentschler et al., "In vivo Robotics during the NEEMO 9 Mission," Medicine Meets Virtual Reality, Feb. 2007, I pg.

Rentschler et al.., "In Vivo Robots for Laparoscopic Surgery," Studies in Health Technology and Infonnatics—Medicine Meets Virtual Reality, ISO Press, Newport Beach, CA, 2004a, 98: 316-322.

Rentschler et al., "Mechanical Design of Robotic In Vivo Wheeled Mobility," ASME Journal of Mechanical Design, 2006a, pp. I-II.

Rentschler et al., "Mobile In Vivo Camera Robots Provide Sole Visual Feedback for Abdominal Exploration and Cholecystectomy," Journal of Surgical Endoscopy, 20-I: 135-138, 2006b.

Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.

Rentschler et al., "Modeling, Analysis, and Experimental Study of In Vivo Wheeled Robotic Mobility," IEEE Transactions on Robotics, 22 (2): 308-321, 2005c.

Rentschler et al., "Natural Orifice Surgery with an Endoluminal Mobile Robot," The Society of American Gastrointestinal Endoscopic Surgeons, Dallas, TX, Apr. 2006d, 14 pp.

Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.

Rentschler et al., "Toward In Vivo Mobility," Studies in Health Technology and Infonnatics—Medicine Meets Virtual Reality, ISO Press, Long Beach, CA, 2005a, III: 397-403.

Response to Rule 312 Amendment in related case U.S. Appl. No. 11/695,944, dated Jan. 12, 2009, 2 pp.

Riviere et al., "Toward Active Tremor Canceling in Handheld Microsurgical Instruments," IEEE Transactions on Robotics and Automation, Oct. 2003, 19(5): 793-800.

Rosen et al., "Force Controlled and Teleoperated Endoscopic, Grasper for Minimally Invasive Surgery-Experimental Performance Evaluation," IEEE Transactions of Biomedical Engineering, Oct. 1999; 46(10): 1212-1221.

Rosen et al., "Objective Laparoscopic Skills Assessments of Surgical Residents Using Hidden Markov Models Based on Haptic Information and Tool/Tissue Interactions," Studies in Health Technology and Infonnatics-Medicine Meets Virtual Reality, Jan. 2001, 7 pp.

Rosen et al., "Spherical Mechanism Analysis of a Surgical Robot for Minimally Invasive Surgery—Analytical and Experimental Approaches," Studies in Health Technology and Infonnatics—Medicine Meets Virtual Reality, pp. 442-448, Jan. 2005.

Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.

Rosen et al., "The Blue Dragon—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.

Ruurda et al., "Robot-Assisted surgical systems: a new era in laparoscopic surgery," Ann R. Coll Surg Engl., 2002; 84: 223-226.

Ruurda et al., "Feasibility of Robot-Assisted Laparoscopic Surgery," Surgical Laparoscopy, Endoscopy & Percutaneous Techniques, 2002; 12(1):41-45.

Sackier et al., "Robotically assisted laparoscopic surgery," Surgical Endoscopy, 1994; 8: 63-66.

(56) References Cited

OTHER PUBLICATIONS

Salky, "What is the Penetration of Endoscopic Techniques into Surgical Practice?" Digestive Surgery, 2000; 17:422-426.
Satava, "Surgical Robotics: The Early Chronicles," Surgical Laparoscopy, Endoscopy & Percutaneous Techniques, 2002; 12(1): 6-16.
Schippers et al., (1996) "Requirements and Possibilities of Computer-Assisted Endoscopic Surgery," In: Computer Integrated Surgery: Technology and Clinical Applications, pp. 561-565.
Schurr et al., "Robotics and Telemanipulation Technologies for Endoscopic Surgery," Surgical Endoscopy, 2000; 14: 375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fantastic Voyage: Smart Pill to Expand Testing," http://www.smartpilldiagnostics.com, Apr. 13, 2005, 1 pg.
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al.., "Long-term Pain: Less Common After Laparoscopic than Open Cholecystectomy," British Journal of Surgery, 1994; 81: 1368-1370.
Strong, et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-287.
Tendick et al.. (1993), "Sensing and Manipulation Problems in Endoscopic Surgery: Experiment, Analysis, and Observation," Presence 2( 1): 66-81.
Tendick et al., "Applications of Micromechatronics in Minimally Invasive Surgery," IEEE/ASME Transactions on Mechatronics, 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
Way et al., (editors), "Fundamentals of Laparoscopic Surgery," Churchill Livingstone Inc., 1995, 14 pp.
Wolfe et al., "Endoscopic Cholecystectomy: An analysis of Complications," Arch. Surg. Oct. 1991; 126: 1192-1196.
Worn et al., "Espirit Project No. 33915: Miniaturised Robot for Micro Manipulation (MINIMAN)", Nov. 1998; http://www.ipr.ira.ujka.de/-microbot/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy a Breakthrough Diagnostic Tool for Small Intestine Imagining," vol. 25, No. 1, Gastroenterology Nursing, pp. 24-27.
International Search Report and Written Opinion of international application No. PCT/US2010/061137, mailed Feb. 11, 2011, 10 pp.
Abbou et al., "Laparoscopic Radical Prostatectomy with a Remote Controlled Robot," The Journal of Urology, Jun. 2001, 165: 1964-1966.
Glukhovsky et al.., "The development and application of wireless capsule endoscopy," Int. J. Med. Robot. Comput. Assist. Surgery, 2004; I (1): 114-123.
Gong et al., Wireless endoscopy, Gastrointestinal Endoscopy 2000; 51(6): 725-729.

Hanly et al., "Value of the SAGES Learning Center in introducing new technology," Surgical Endoscopy, 2004; 19 (4): 477-483.
International Search report and Written Opinion from international application No. PCT/US2012/41911, mailed Mar. 13, 2013.
International Search Report and Written Opinion from international application No. PCT/US12/46274, mailed Sep. 25, 2012.
International Search Report and Written Opinion from international application No. PCT/US2007/089191, mailed Nov. 10, 2008, 20 pp.
"International Search Report and Written Opinion from international application No. PCT/US07/14567, mailed Apr. 28, 2008, 19 pp."
International Search Report and Written Opinion of international application No. PCT/US2008/069822, mailed Aug. 5, 2009, 12 pp.
International Search Report and Written Opinion of international application No. PCT/US2008/073334, mailed Jan. 12, 2009, 11 pp.
International Search Report and Written Opinion of international application No. PCT/US2008/073369, mailed Nov. 12, 2008, 12 pp.
International Search Report and Written Opinion issued in PCT/US11/46809, mailed Dec. 8, 2011.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine model," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001; pp. 94-104.
Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.
Kazemier et al. (1998), "Vascular Injuries During Laparoscopy," J. Am. Coli. Surg. 186(5): 604-5.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136:180-184.
Leggett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
MacFarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.

(56) References Cited

OTHER PUBLICATIONS

Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, I/4-inch VGA NTSC/PAL CMOS Digital Image Sensor, 98 pp.
Midday Jeff et al., "Material Handling System for Robotic natural Orifice Surgery", Proceedings of the 2011 Design of medical Devices Conference, Apr. 12-14, 2011, Minneapolis, MN, 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Office Action dated Apr. 17, 2007, received in related case U.S. Appl. No. 11/552,379, 5 pp.
Office Action dated Oct. 29, 2007, received in related case U.S. Appl. No. 11/695,944, 5pp.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13(3): 181-184.
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Applicant Amendment after Notice of Allowance under Rule 312, filed Aug. 25, 2008, in related case U.S. Appl. No. 11/695,944, 6pp.
Applicant Response to Office Action dated Apr. 17, 2007, in related case U.S. Appl. No. 11/552,379, filed Aug. 8, 2007, 7 pp.
Applicant Response to Office Action dated Aug. 18, 2006, in related case U.S. Appl. No. 11/398,174, filed Nov. 7, 2006, 8pp.
Applicant Response to Office Action dated Aug. 21, 2006, in related case U.S. Appl. No. 11/403,756, filed Nov. 21, 2006, 52pp.
Applicant Response to Office Action dated Oct. 29, 2007, in related case U.S. Appl. No. 11/695,944, filed Jan. 22, 2008, 6pp.
Atmel 80C5X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 2-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al., (2003), "Measuring Forces in Liver Cutting: New Equipment and Experimenal Results," Annals of Biomedical Engineering 31: 1372-1382.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving in Vivo Robot Visioin Quality," from the Proceedings of Medicine Meets Virtual Realtiy, Long Beach, CA, Jan. 26-29, 2005. 1 pg.
Dumpert et al., "Stereoscopic In Vivo Surgical Robots," IEEE Sensors Special Issue on In Vivo Sensors for Medicine, Jan. 2007, 10 pp.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Flynn et al., "Tomorrow's Surgery: micromotors and microbots for minimally invasive procedures," Minimally Invasive Surgery & Allied Technologies.
Franklin et al., "Prospective Comparison of Open vs. Laparoscopic Colon Surgery for Carcinoma: Five-Year Results," Dis Colon Rectum, 1996; 39: S35-S46.
Franzino, "The Laprotek Surgical System and the Next Generation of Robotics," Surg Clin North Am, 2003 83(6).
Fraulob et al., "Miniature assistance module for robot-assisted heart surgery," Biomed. Tech. 2002, 47 Suppl. 1, Pt. 1: 12-15.

(56) References Cited

OTHER PUBLICATIONS

Fukuda et al., "Mechanism and Swimming Experiment of Micro Mobile Robot in Water," Proceedings of the 1994 IEEE International Conference on Robotics and Automation, 1994: 814-819.

Fukuda et al., "Micro Active Catheter System with Multi Degrees of Freedom," Proceedings of the IEEE International Conference on Robotics and Automation, May 1994, pp. 2290-2295.

Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.

Grady, "Doctors Try New Surgery for Gallbladder Removal," The New York Times, Apr. 20, 2007, 3 pp.

Guber et al., "Miniaturized Instrumetn Systems for Minimally Invasive Diagnosis and Therapy," Biomedizinishe Technic. 2002, Band 47, Erganmngsband 1.

Palm, William, "Rapid Prototyping Primer" May 1998 (revised Jul. 30, 2002) (http://www.me.psu.edu/lamancusa/rapidpro/primer/chapter2.htm).

\* cited by examiner

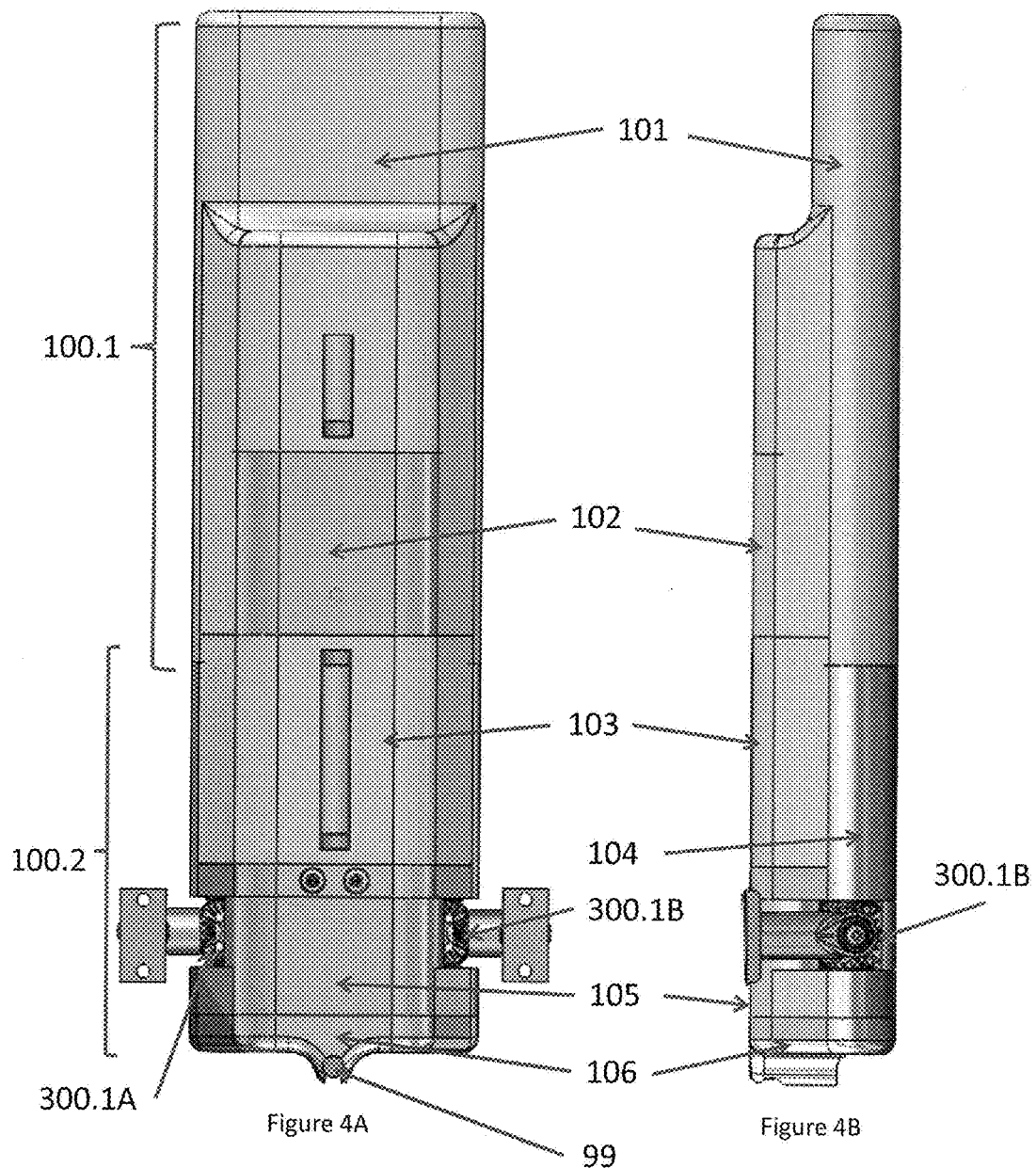

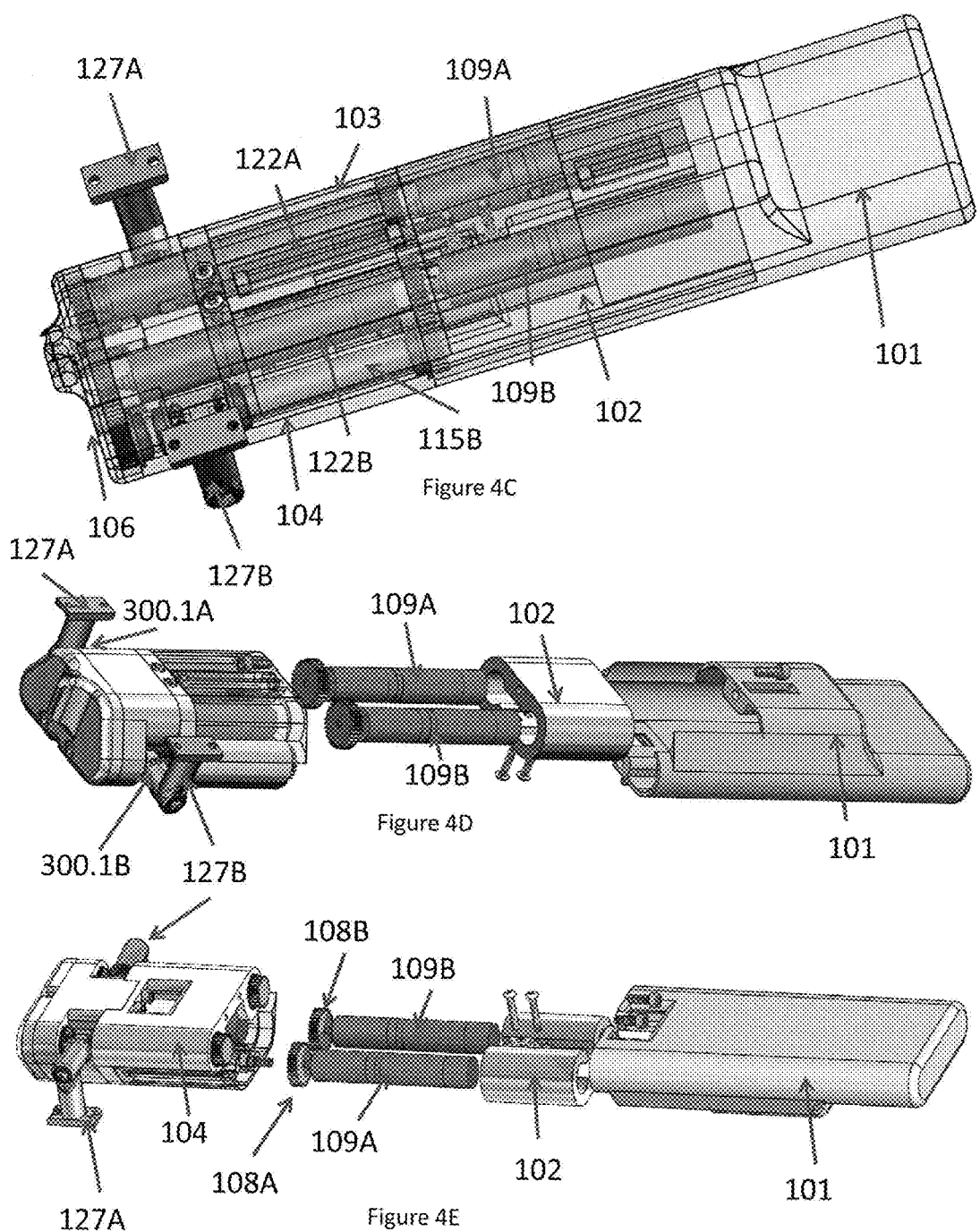

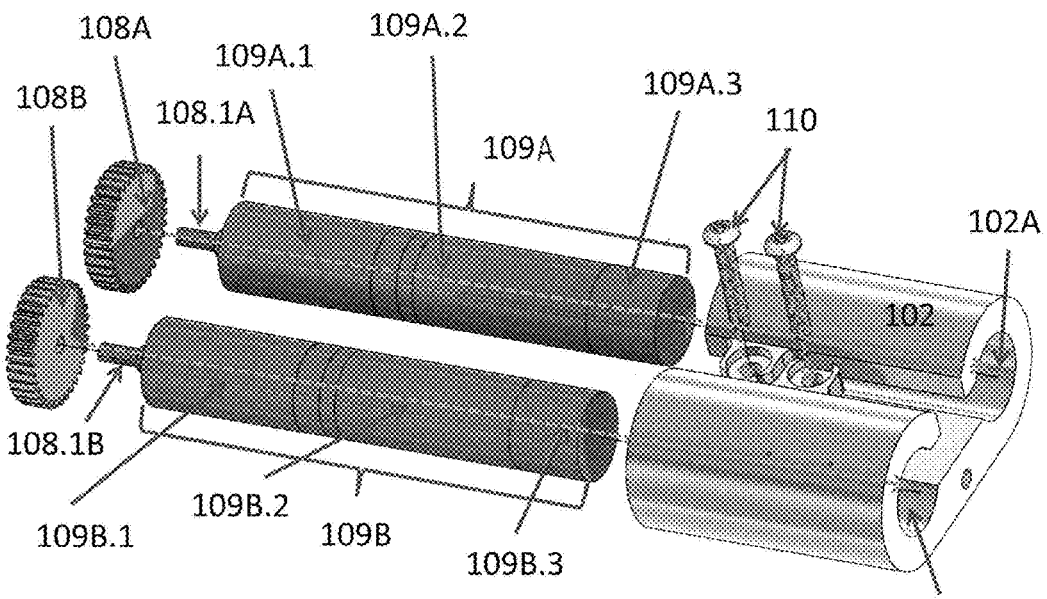
Figure 6A
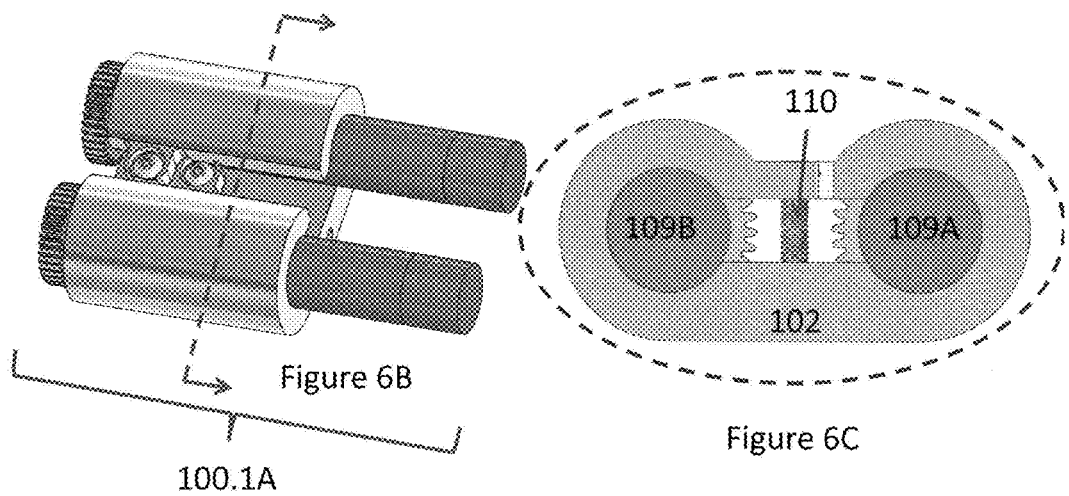
Figure 6B
Figure 6C

SINGLE SITE ROBOTIC DEVICE AND RELATED SYSTEMS AND METHODS

CROSS REFERENCE TO RELATED APPLICATIONS

This application claims priority from U.S. Provisional Application 61/640,879, filed May 1, 2012, and entitled "Single Site Robotic Device and Related Systems and Methods," which is hereby incorporated herein by reference in its entirety.

GOVERNMENT SUPPORT

These inventions were made with government support under at least one of the following grants: Grant Nos. NNX10AJ26G and NNX09AO71A, awarded by the National Aeronautics and Space Administration; Grant Nos. W81XWH-08-2-0043 and W81XWH-09-2-0185, awarded by U.S. Army Medical Research and Material Command; Grant No. DGE-1041000, awarded by the National Science Foundation; and Grant No. 2009-147-SC1, awarded by the Experimental Program to Stimulate Competitive Research at the National Aeronautics and Space Administration. Accordingly, the government has certain rights in the invention.

TECHNICAL FIELD

The embodiments disclosed herein relate to various medical devices and related components, including robotic and/or in vivo medical devices and related components. Certain embodiments include various robotic medical devices, including robotic devices that are disposed within a body cavity and positioned using a support component disposed through an orifice or opening in the body cavity. Further embodiment relate to methods of operating the above devices.

BACKGROUND

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

BRIEF DESCRIPTION OF THE DRAWINGS

FIG. 4A is a schematic view of the robotic medical device body from the top, according to one embodiment.

FIG. 4B is a schematic view of the robotic medical device body from the side, according to the embodiment of FIG. 4A.

FIG. 4C is a cutaway perspective schematic view of a robotic medical device body, according to the embodiment of FIG. 4A.

FIG. 4D is a perspective exploded schematic view of a robotic medical device body, according to the embodiment of FIG. 4A.

FIG. 4E is another exploded schematic view of a robotic medical device body, according to the embodiment of FIG. 4A.

FIG. 4E is an end-long see-through schematic view of a robotic medical device body, according to the embodiment of FIG. 4A.

FIG. 6A is a top perspective exploded schematic of the internal components of body of a robotic device, according to one embodiment.

FIG. 6B is a top perspective separated schematic of the internal components of a robotic device, according to the embodiment of FIG. 6A.

FIG. 6C is an endlong schematic of the internal components of a robotic device, along the section line of FIG. 6B according to the embodiment of FIG. 6B.

DETAILED DESCRIPTION

Figure 1:
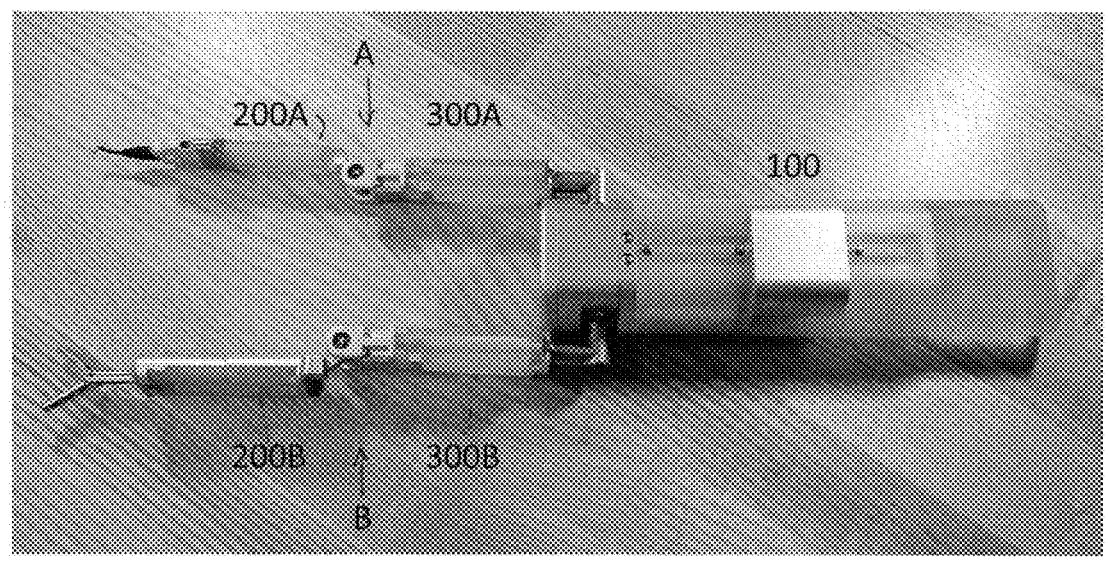
FIG. 1 is a top perspective view of a robotic surgical system according to one embodiment.

The various embodiments disclosed or contemplated herein relate to surgical robotic devices, systems, and methods. More specifically, various embodiments relate to various medical devices, including robotic devices and related methods and systems. Certain implementations relate to such devices for use in laparo-endoscopic single-site (LESS) surgical procedures.

It is understood that the various embodiments of robotic devices and related methods and systems disclosed herein can be incorporated into or used with any other known medical devices, systems, and methods. For example, the various embodiments disclosed herein may be incorporated into or used with any of the medical devices and systems disclosed in copending U.S. application Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966,741 (filed on Dec. 28, 2007 and entitled "Methods, Systems, and Devices for Surgical Visualization and Device Manipulation"), 61/030,588 (filed on Feb. 22, 2008), Ser. No. 12/171,413 (filed on Jul. 11, 2008 and entitled "Methods and Systems of Actuation in Robotic Devices"), Ser. No. 12/192,663 (filed Aug. 15, 2008 and entitled Medical Inflation, Attachment, and Delivery Devices and Related Methods"), Ser. No. 12/192,779 (filed on Aug. 15, 2008 and entitled "Modular and Cooperative Medical Devices and Related Systems and Methods"), Ser. No. 12/324,364 (filed Nov. 26, 2008 and entitled "Multifunctional Operational Component for Robotic Devices"), 61/640,879 (filed on May 1, 2012), Ser. No. 13/493,725 (filed Jun. 11, 2012 and entitled "Methods, Systems, and Devices Relating to Surgical End Effectors"), Ser. No. 13/546,831 (filed Jul. 11, 2012 and entitled "Robotic Surgical Devices, Systems, and Related Methods"), 61/680,809 (filed Aug. 8, 2012), Ser. No. 13/573,849 (filed Oct. 9, 2012 and entitled "Robotic Surgical Devices, Systems, and Related Methods"), and Ser. No. 13/738,706 (filed Jan. 10, 2013 and entitled "Methods, Systems, and Devices for Surgical Access and Insertion"), and U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), and U.S. Pat. No. 8,179,073 (issued May 15, 2011, and entitled "Robotic Devices with Agent Delivery Components and Related Methods"), all of which are hereby incorporated herein by reference in their entireties.

Certain device and system implementations disclosed in the applications listed above can be positioned within a body cavity of a patient in combination with a support component similar to those disclosed herein. An "in vivo device" as used herein means any device that can be positioned, operated, or controlled at least in part by a user while being positioned within a body cavity of a patient, including any device that is coupled to a support component such as a rod or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain embodiments provide for insertion of the present invention into the cavity while maintaining sufficient insufflation of the cavity. Further embodiments minimize the physical contact of the surgeon or surgical users with the present invention during the insertion process. Other implementations enhance the safety of the insertion process for the patient and the present invention. For example, some embodiments provide visualization of the present invention as it is being inserted into the patient's cavity to ensure that no damaging contact occurs between the system/device and the patient. In addition, certain embodiments allow for minimization of the incision size/length. Further implementations reduce the complexity of the access/insertion procedure and/or the steps required for the procedure. Other embodiments relate to devices that have minimal profiles, minimal size, or are generally minimal in function and appearance to enhance ease of handling and use.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

Figure 2:
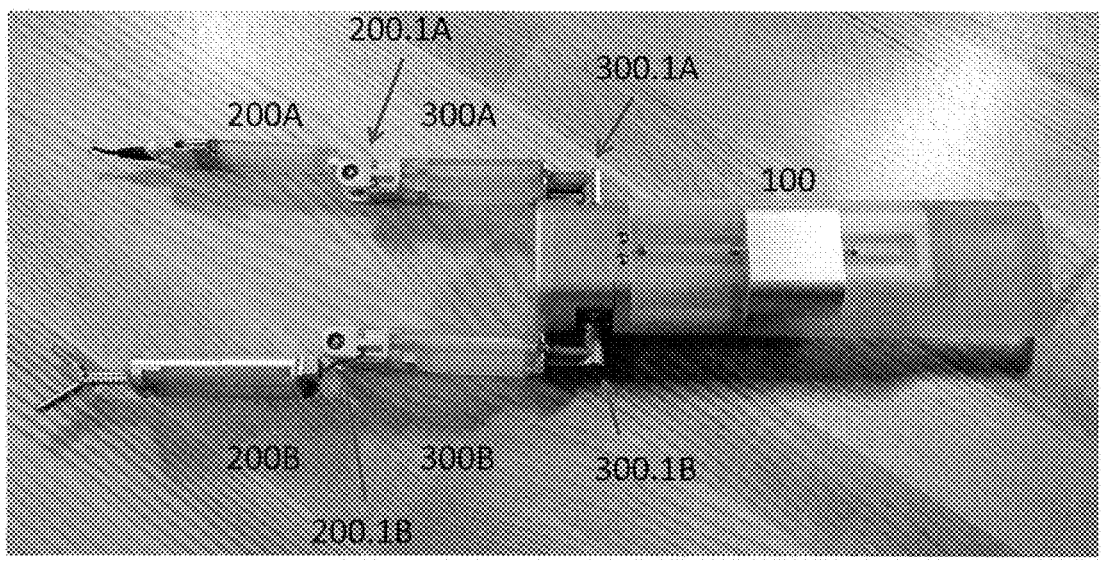
FIG. 2 is the same perspective view of the device of FIG. 1.
Figure 3:
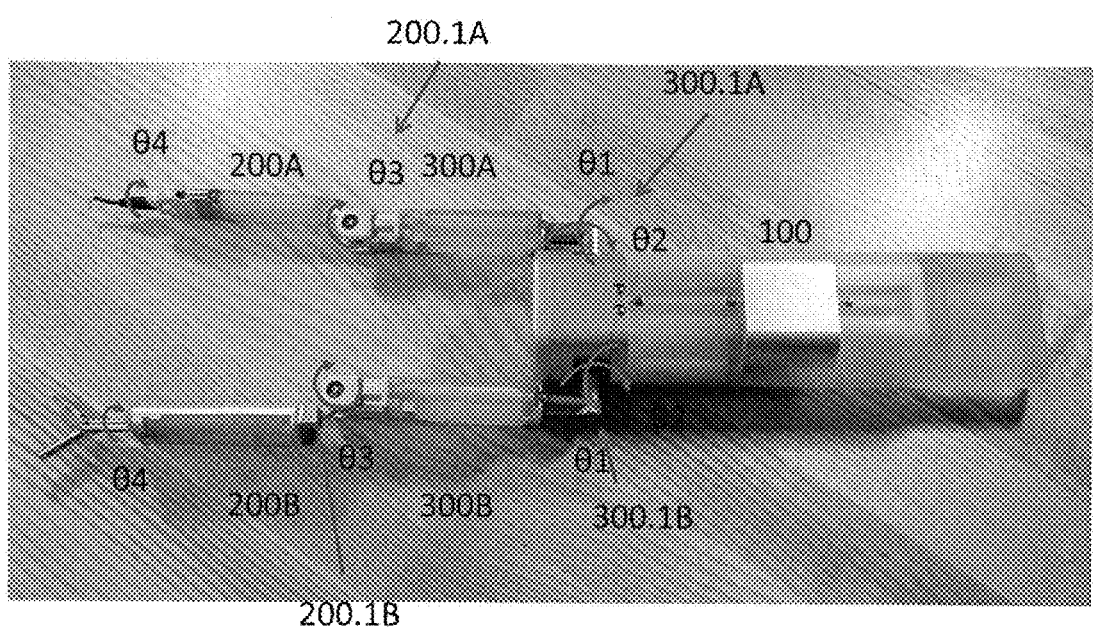
FIG. 3 is the same perspective view of the device of FIG. 1.

An exemplary embodiment of a robotic device is depicted in FIGS. 1, 2, and 3. The device has a main body, 100, a right arm A, and a left arm B. As best shown in FIG. 2, each of the left B and right A arms is comprised of 2 segments: an upper arm (or first link) 300A, 300B and a forearm (or second link) 200A, 200B, thereby resulting in each arm A, B having a shoulder joint (or first joint) 300.1A, 300.1B and an elbow joint (or second joint) 200.1A, 200.1B. As best shown in FIGS. 2-32, in certain implementations, each of the left arm B and right arm A is capable of four degrees of freedom. The left shoulder joint 300.1B and right shoulder joint 300.1A have intersecting axes of rotation: shoulder yaw ($\theta 1$) and shoulder pitch ($\theta 2$). The elbow joints 200.1A, 200.1B contribute a degree of freedom—elbow yaw ($\theta 3$)— and the end effectors do as well: end effector roll ($\theta 4$).

Figure 4F:
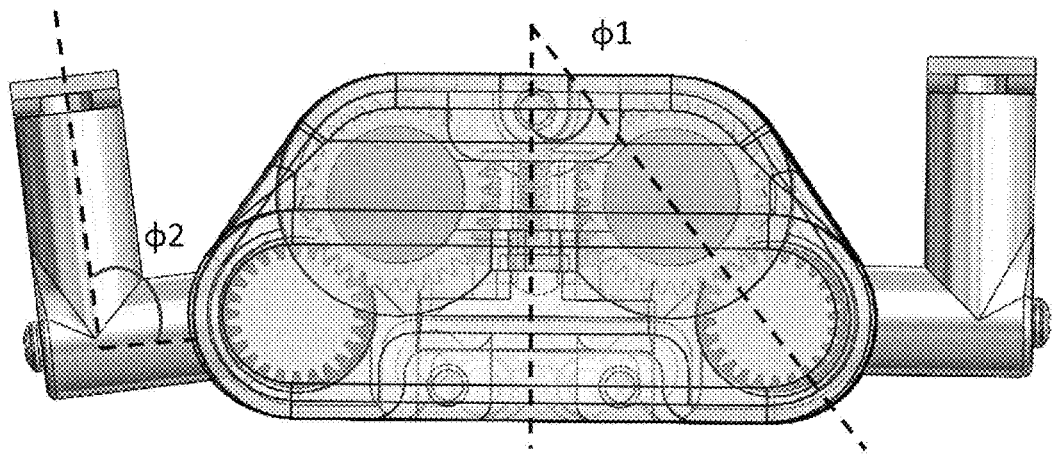
FIG. 4F is another cutaway perpective schematic view of a robotic medical device body, according to the embodiment of FIG. 4A.

FIGS. 4A, 4B, 4C, 4D, 4E, 4F, 4G, and 4H depict the device body 100 according to an exemplary embodiment. More specifically, FIG. 4A depicts a front view of the body 100, while FIG. 4B depicts a side view. In addition, FIGS. 4C, 4D, 4E, 4F, 4G, and 4H depict various perspectives of the device body 100 in which various internal components of the body 100 are visible.

Figure 4G:
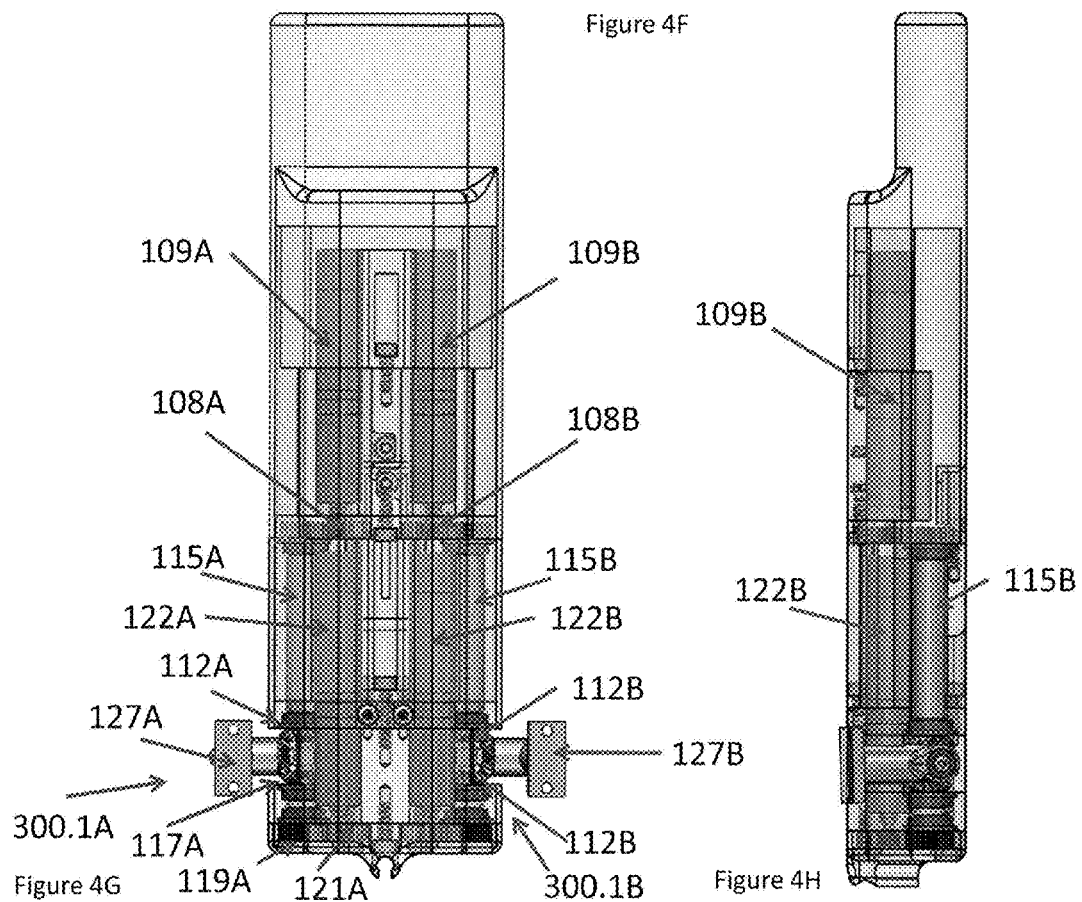
FIG. 4G is a top-down see-through schematic view of a robotic medical device body, according to the embodiment of FIG. 4A.
Figure 4H:
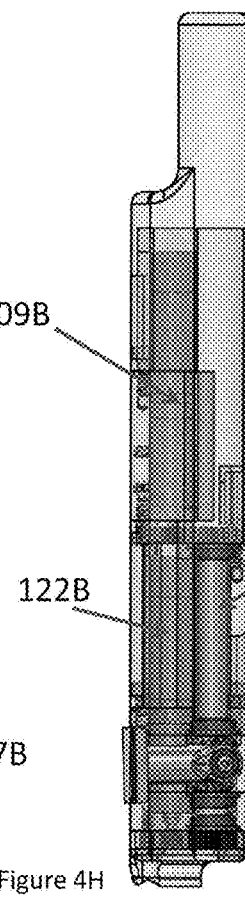
FIG. 4H is a see-through schematic side view of a robotic medical device body, according to the embodiment of FIG. 4A.

The body 100 contains four motors which control shoulder yaw ($\theta 1$) and shoulder pitch ($\theta 2$) for the right and left arms A, B. More specifically, as best shown in FIGS. 4C, 4G, and 13D, the proximal right motor 109A and distal right motor 122A control shoulder yaw (θ1) and shoulder pitch (θ2) for the right shoulder 300.1A, while the proximal left motor 109B and distal left motor 122B control shoulder yaw (θ1) and shoulder pitch (θ2) for the left shoulder 300.1B. This discussion will focus on the right shoulder 300.1A and arm A, but it is understood that a similar set of components are coupled in a similar fashion to control the yaw and pitch of the left shoulder 300.1B and left arm B.

As best shown in FIG. 4G (and as will be explained in further detail elsewhere herein), the proximal right motor 109A is operably coupled to the right shoulder subassembly 127A of the right shoulder 300.1A via gear 108A, which is operably coupled to gear 115.1A on the end of the right spur shaft 115A, and the right bevel gear first right bevel gear at the opposite end of the right spur shaft 115A is operably coupled to the bevel gear 130A of the right shoulder subassembly 127A. In addition, the distal right motor 122A is operably coupled to the right shoulder subassembly 127A via a right distal spur gear 121A, which is operably coupled to a gear 119A, which is operably coupled to bevel gear second right bevel gear 117A, which is operably coupled to the bevel gear 130A of the right shoulder subassembly 127A. The proximal right motor 109A and distal right motor 122A operate together to control both the shoulder yaw (θ1) and shoulder pitch (θ2) for the right shoulder 300.1A by rotating the first right bevel gear and second right bevel gear at predetermined directions and speeds as will be described in further detail below.

In one embodiment, the four motors 109A, 109B, 122A, 122B, along with the motors in the arms as described elsewhere herein, are brushed direct current (DC) motors with integrated magnetic encoders and planetary gearheads. According to various embodiments, the motors used in the device can vary in size depending on the particular device embodiment and the location and/or use of the motor, with the size ranging in diameter from about 6 mm to about 10 mm Alternatively, any known motors or other devices for converting electrical energy into rotational motion can be used.

Figure 5A:
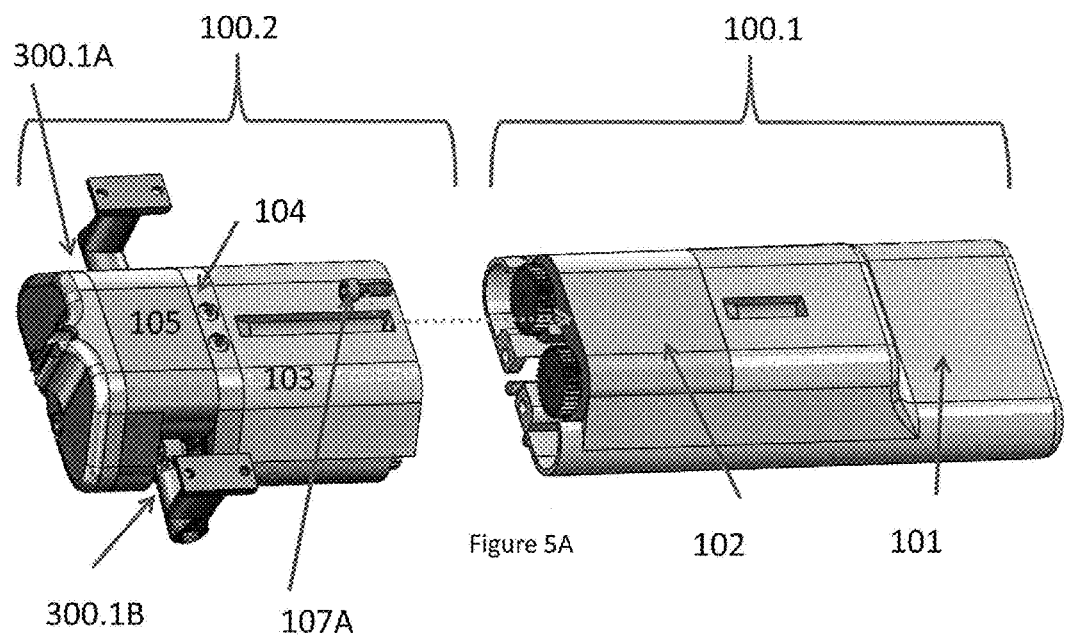
FIG. 5A is a top perspective exploded schematic of the body of a robotic device, according to one embodiment.

As best shown in FIGS. 4A and 4B, according to one implementation, the body 100 has a plurality of segments that result in separate housings or subassemblies that are coupled together. In the implementation depicted in FIGS. 4A and 4B, there are six segments, but other numbers are possible. These segments 101, 102, 103, 104, 105, and 106 create housings that provide protection for internal electronics and support for internal components, including motors and drivetrain components. In the implementation shown in FIGS. 4A and 4B, first segment 101 is configured to be coupled with second segment 102 such that second segment 102 is positioned at least partially within segment first 101, thereby creating first housing 100.1 as shown in FIGS. 4A, 4B, and 5A. Third segment 103, fourth segment 104, and fifth segment 105 are also coupled together to create second housing 100.2 as shown in FIGS. 4A, 4B, and 5A. Finally, first housing 100.1 and second housing 100.2 are coupled together as best shown in FIG. 5A. The segments, housings, and their assembly into the body 100 are discussed in further detail below.

As best shown in FIG. 4A, in certain embodiments, the distal end (or bottom) of the body 100 can also have a camera 99. In the implementation shown in FIG. 4A, the camera 99 is a single fixed camera 99 positioned in direct line of sight of the surgical workspace. Alternatively, the body 100 could have multiple cameras operating together to provide stereoscopic (3D) vision. In a further alternative, any known camera or set of cameras for use in medical devices could be used. In further embodiments, the body 100 can also have a lighting system such as LEDs and/or fiber optic lights to illuminate the body cavity and/or the surgical workspace.

In one implementation, the plurality of segments 101, 102, 103, 104, 105, 106 are made of a combination of machined aluminum and rapid prototyped plastic. One example of a process using such materials is described in "Rapid Prototyping Primer" by William Palm, May 1998 (revised Jul. 30, 2002), which is hereby incorporated herein by reference in its entirety. Alternatively, it is understood by those skilled in the art that many other known materials for medical devices can be used, including, but not limited to, stainless steel and/or injection molded plastics.

Figure 5B:
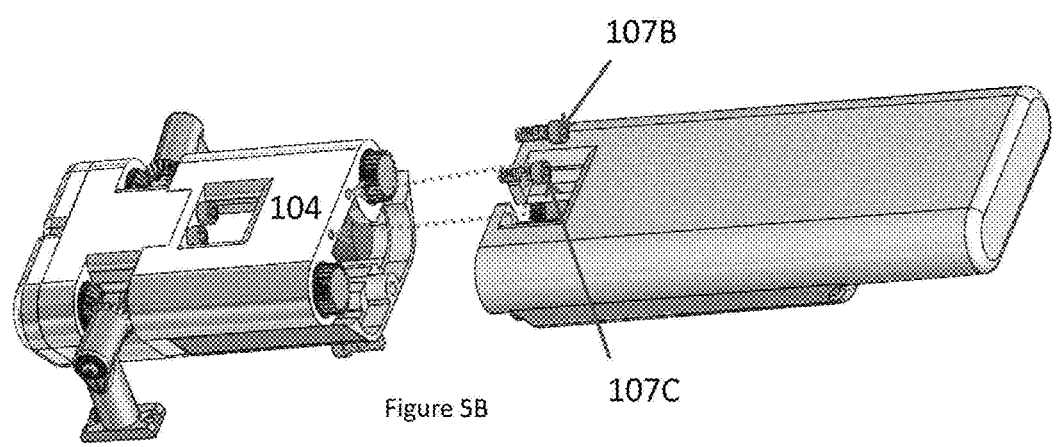
FIG. 5B is a bottom perspective exploded schematic of the body of a robotic device, according to the embodiment of FIG. 5A.

FIGS. 5A and 5B depict the first and second housings 100.1, 100.2. FIG. 5A depicts the front of the first and second housings 100.1, 100.2, while FIG. 5B depicts the back. As best shown in FIGS. 4C-4H in combination with FIGS. 5A and 5B, the proximal right motor 109A and proximal left motor 109B are positioned in the first housing 100.1, while the distal right motor 122A and distal left motor 122B are positioned in the second housing 100.2. the first and second housings 100.1, 100.2 are coupled together using a plurality of threaded members 107A, 107B, 107C as shown. Alternatively, any coupling mechanism can be used to retain the first 100.1 and second housings 100.2 together.

FIGS. 6A, 6B, and 6C depict the second segment 102 and the positioning of the right 109A and left proximal motors 109B within. In this specific embodiment, each of the proximal motors 109A, 109B has a diameter of 10 mm and is made up of three components: the right planetary gearhead 109A.1 and left planetary gearhead 109B.1, the proximal right motor drive component 109A.2, proximal left motor drive component 109B.2, and the right 109A.3 and left encoders 109B.3. It is understood that the right 109A.1 and left 109B.1 planetary gearheads reduce the speed of the proximal motor drive components, 109A.2, 109B.2 and thus increases the output torque. It is further understood that the right 109A.3 and left 109B.3 encoders control the position of the right proximal motor output shaft 108.1A and left proximal motor output shaft 108.1B using electric pulses which can be generated by magnetic, optic, or resistance means. Thus, the right and left encoders 109A.3, 109B.3 provide accurate positioning of the right proximal motor output shaft 108.1A and left proximal motor output shaft 108.1B.

Thus, in certain implementations, each of the proximal right 108A, and proximal left spur gears 108B is used to transmit the rotational motion from the corresponding proximal motor 109A, 109B which further comprises a proximal motor drive component 109A.2, 109B.2 which acts through a planetary gearhead 109A.1, 109B.1). Each proximal spur gear 108A, 108B is rotationally constrained with a "D" shaped geometric feature 108.1A, 108.1B and, in some embodiments, a bonding material such as JB-Weld.

As shown in FIGS. 6A, 6B, and 6C, the second segment 102 has a plurality of partial lumens, in this implementation a right partial lumen 102A and left partial lumen 102B defined within the second segment 102 that have inner walls that do not extend a full 360 degrees. The right and left partial lumens 102A, 102B are configured to receive the right and left proximal motors 109A, 109B. The right and left proximal motors 109A, 109B can be positioned in the right and left partial lumens 102A, 102B as shown in FIGS. 6B, and 6C. In one embodiment, the second segment 102 is configured to allow for the diameter of the walls of the right and left partial lumens 102A, 102B to be reduced after the right and left proximal motors 109A, 109B have been positioned therein, thereby providing frictional resistance to rotationally and translationally secure the right and left proximal motors 109A, 109B within the right and left partial lumens 102A, 102B, thereby creating first subassembly 100.1A. More specifically, the second segment 102 allows for a clamping force to be applied to the right and left proximal motors 109A, 109B by the tightening of the thread members 110. It is understood that the right and left proximal motors 109A, 109B can also be constrained or secured by any other known method or mechanism.

Figure 7A:
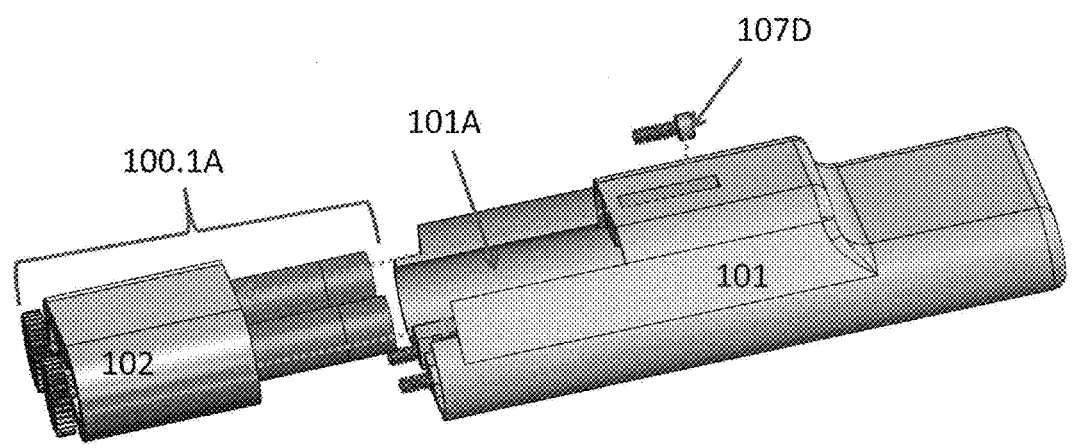
FIG. 7A is a top perspective separated schematic of the internal components and body of a robotic device, according to one embodiment.
Figure 7B:
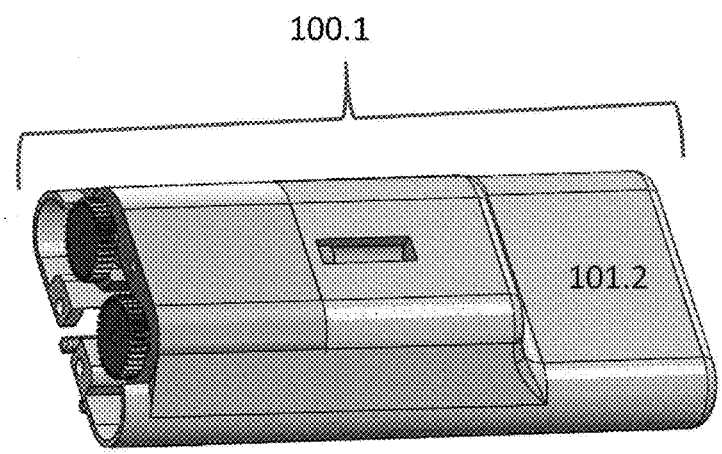
FIG. 7B is an exploded top perspective view of the body of a robotic device, according to the embodiment of FIG. 7A.

FIGS. 7A and 7B show the attachment or coupling of the first subassembly 100.1A with the first segment 101, thereby resulting in the first housing 100.1. First segment 101 has a first segment mating feature 101A defined within the first segment 101 that is configured to receive the first subassembly 100.1A. More specifically, in the embodiment depicted in FIG. 7A, the first segment mating feature 101A is an opening defined in the first segment 101 that mates with the first subassembly 100.1A such that the first subassembly 100.1A fits within the opening and couples with the first segment 101. In one embodiment, the first subassembly 100.1A fits within the first segment mating feature 101A such that the first subassembly 100.1A and the first segment 101 are rotationally constrained with respect to each other. Further, a first threaded member 107D is used to translationally constrain the components.

In accordance with one implementation, the first segment top portion 101.1 of the first segment 101 is configured or shaped to receive an external clamp (such as, for example, a commercially available external clamp available from Automated Medical Products Corp. The clamp can be attached to the first segment top portion 101.1 to easily and securely attach the clamp to the body 100.

Figure 8A:
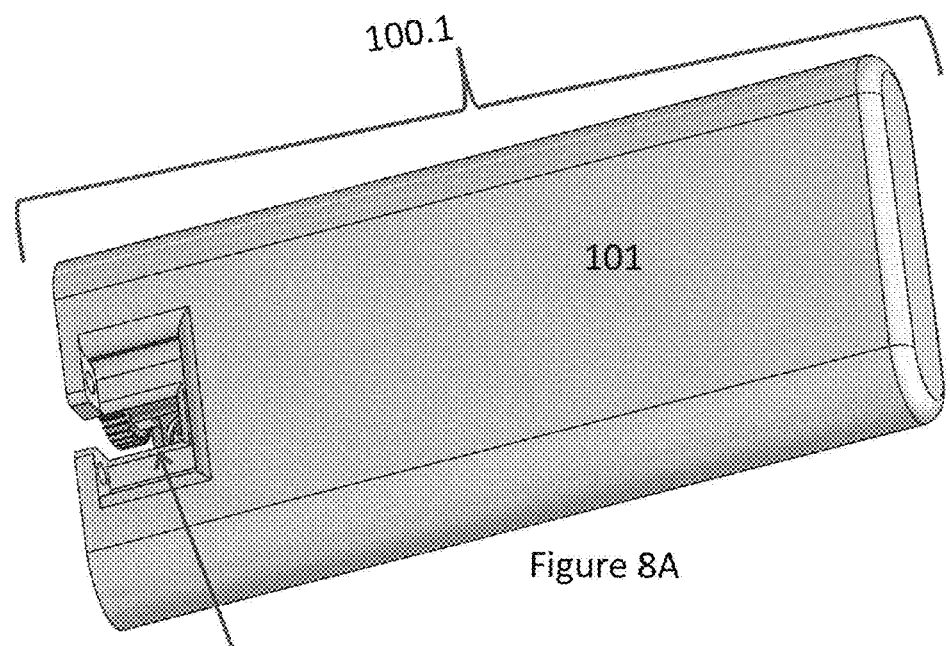
FIG. 8A is a bottom perspective view of the internal components and body of a robotic device, according to one embodiment.
Figure 8B:
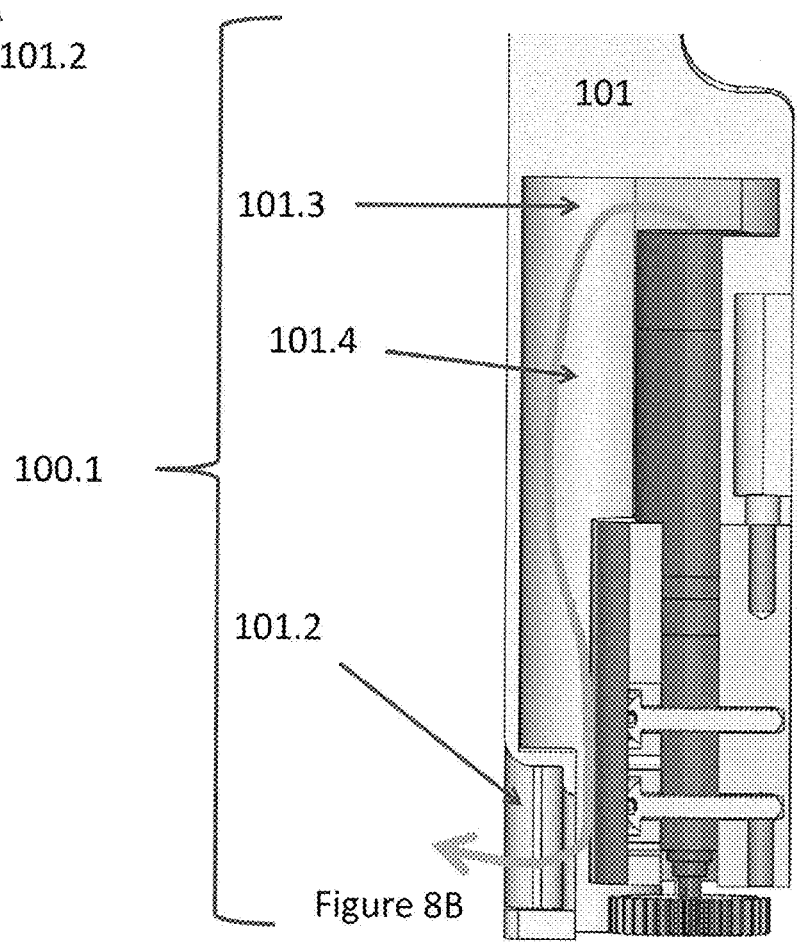
FIG. 8B is a sectional view of the body of a robotic device showing internal wiring, according to the embodiment of FIG. 8A.

As shown in FIGS. 8A and 8B, the first housing 100.1 can have additional features, according to one embodiment. More specifically, the first segment 101 can have a notch or opening 101.2 defined at a bottom back portion of the first segment 101 that provides an exit site for cabling/wiring 101.4 coupled to at least one of the right and left proximal motors 109A, 109B disposed within the first housing 100.1. According to one embodiment, the opening 101.2 can provide strain relief for the cabling/wiring 101.4 to maintain the integrity of the electrical/electronic connections. That is, the opening 101.2 can provide a clamping feature that clamps or otherwise secures all of the cabling/wiring 101.4 that extend through the opening, such that any external forces applied to the cabling/wiring 101.4 do not extend past the opening 101.2, thereby preventing undesirable forces or strain on the connections of any of those cables/wires 101.4 to any internal components inside the first housing 100.1. The clamping feature results from the coupling of first 100.1 and second housings 100.2 as best shown in FIG. 5B. The urging of all the cabling/wiring 101.4 into the opening 101.2 for purposes of allowing for coupling of the housings 100.1 and 100.2 results in a "clamping" of the cabling/wiring 101.4 resulting from the frictional restriction of the cabling/wiring 101.4 in the opening 101.2. In some alternative embodiments, the opening 101.2 can also be filled prior to use with silicon or some other means of sealing against liquid contaminants, body fluids, etc., which can also provide additional strain relief similar to the clamping feature described above. In addition, the first housing 100.1 can also have a cavity 101.3 defined within the first housing 100.1 that allows sufficient clearance for the cabling/wiring 101.4 to extend from at least one of the right and left proximal motors 109A, 109B and exit through opening 101.2.

Figure 9A:
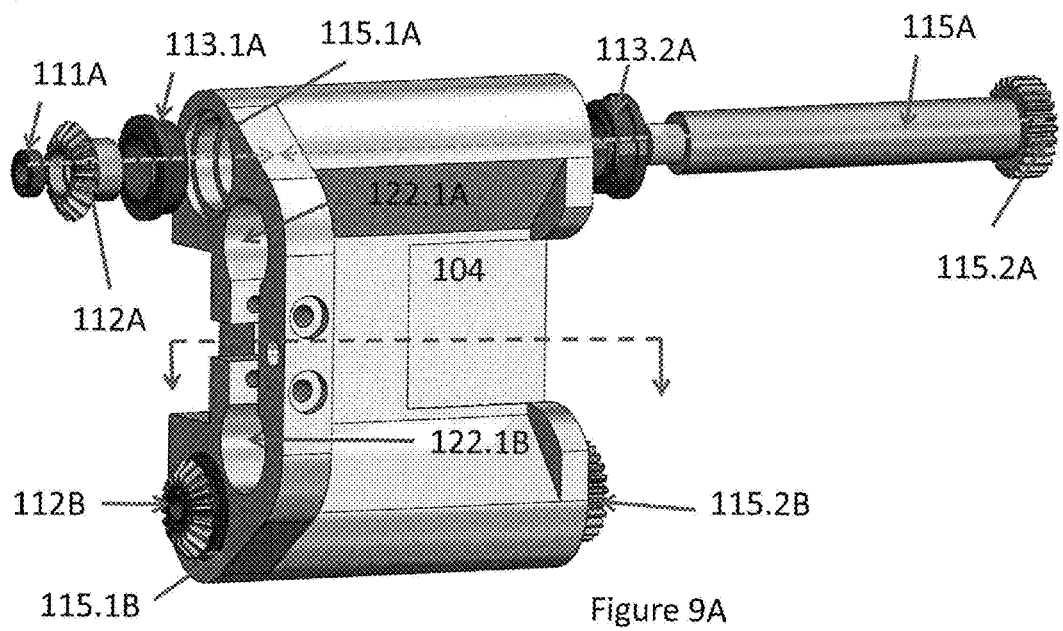
FIG. 9A is another exploded perspective view of internal components of a robotic device, according to one embodiment.
Figure 9B:
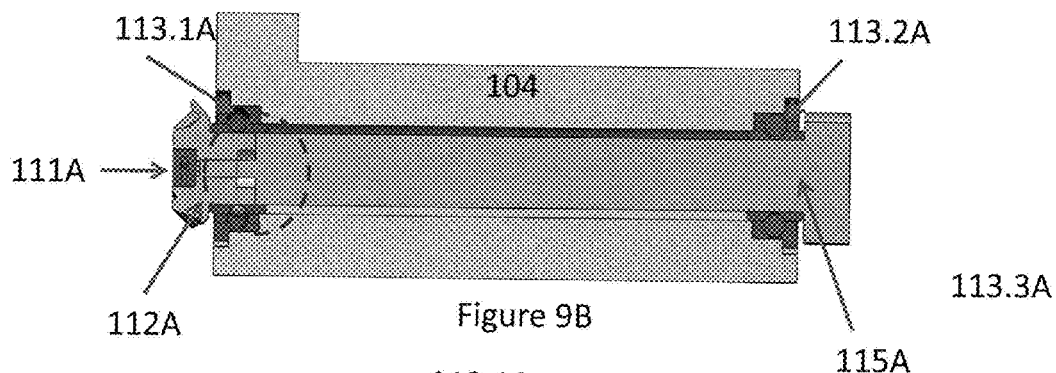
FIG. 9B is a sectional view of the body of a robotic device, according to the embodiment of FIG. 9A.
Figure 9C:
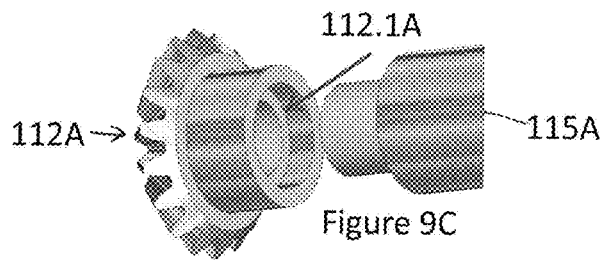
FIG. 9C is a close exploded view of bevel gear and spur shaft of a robotic device, according to the embodiment of FIG. 9A.

FIGS. 9A, 9B, and 9C depict the fourth segment 104, which is a component of the second housing 100.2 discussed above and depicted in FIGS. 5A and 5B. The fourth segment 104 has right 115.1A, and left fourth segment lumens 115.1B defined in the fourth segment 104 that are configured to receive the right proximal spur shaft 115A and left proximal spur shaft 115B, both of which are part of the drive trains that operably couple the right and left proximal motors 109A, 109B to the right and left shoulder subassemblies 127A, 127B that constitute the right 300.1A and left 300.1B shoulders of the device. The fourth segment 104 also has right and left holes 122.1A, 122.1B defined in the fourth segment 104. These holes 122.1A, 122.1B are discussed in further detail in relation to FIGS. 11A and 11B below. While the drive train that includes the right proximal spur shaft 115A will be discussed in detail in this paragraph, it is understood that the drive train that includes the left proximal spur shaft 115B has the same components that are coupled and function in the same manner. As discussed above with respect to FIGS. 4C and 4G, the right proximal spur shaft 115A is configured to be disposed through the right lumen 115.1A of the fourth segment 104. It has a first right driven gear 115.2A at one end and is coupled to a first right bevel gear 112A at the other. In addition, as best shown in FIGS. 9A and 9B, a first right ball bearing 111A is positioned within an opening or recess in the first right bevel gear 112A and is contacted only on its outer race by the inner wall of the opening in the first right bevel gear 112A. In the finished assembly, this contact will provide appropriate preload to this bearing. It is understood by those of ordinary skill in the art that "bearing preload" is a term and concept that is well known in the art as a mechanism or method by which to improve manufacturing tolerances from the ball bearing by applying a constant axial stress.

Further, a second right ball bearing 113.1A is positioned on or around the hub of the first right bevel gear 112A so that its inner race is the only contact with the hub of the first right bevel gear 112A. A third ball bearing 113.2A is positioned on or around the right proximal spur shaft 115A in a similar manner and further is positioned in a right bore hole 113.3A in the right lumen 115.1A, as best shown in FIG. 9B. According to one embodiment, first right bevel gear 112A is coupled to the spur shaft 115A via a threaded coupling (not shown). That is, the first right bevel gear 112A has a bevel gear lumen 112.1A as best shown in FIG. 9C that contains internal threads (not shown) while the spur shaft 115A has external threads (not shown) defined on an outer surface at the end of the shaft 115A that comes into contact with first right bevel gear 112A. In one implementation, a thread locker is used to permanently affix the first right bevel gear 112A to the right proximal spur shaft 115A. According to one particular exemplary embodiment, the thread locker can be Loctite, which is commercially available from Henkel Corp. in Dusseldorf, Germany. As such, the second and third ball bearings 113.1A, 113.2A contact the inner walls of the lumen 115.1A on their outer races and contact the outer surfaces of the first right bevel gear 112A and the right proximal spur shaft 115A with their inner races. Further, in one embodiment, the act of coupling the internal threads in the bevel gear lumen 112.1A with the external threads on the outer surface of the spur shaft 115A preloads the second and third ball bearings 113.1A, 113.2A.

Figure 10A:
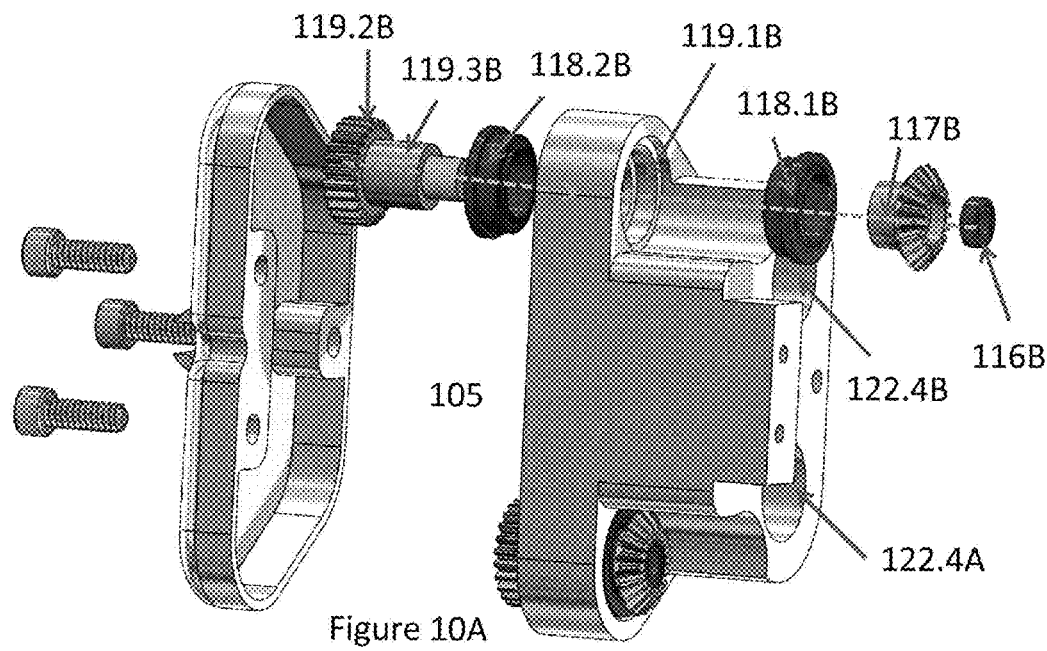
FIG. 10A is an perspective exploded view of the body segments of a robotic device, according to another embodiment.
Figure 10B:
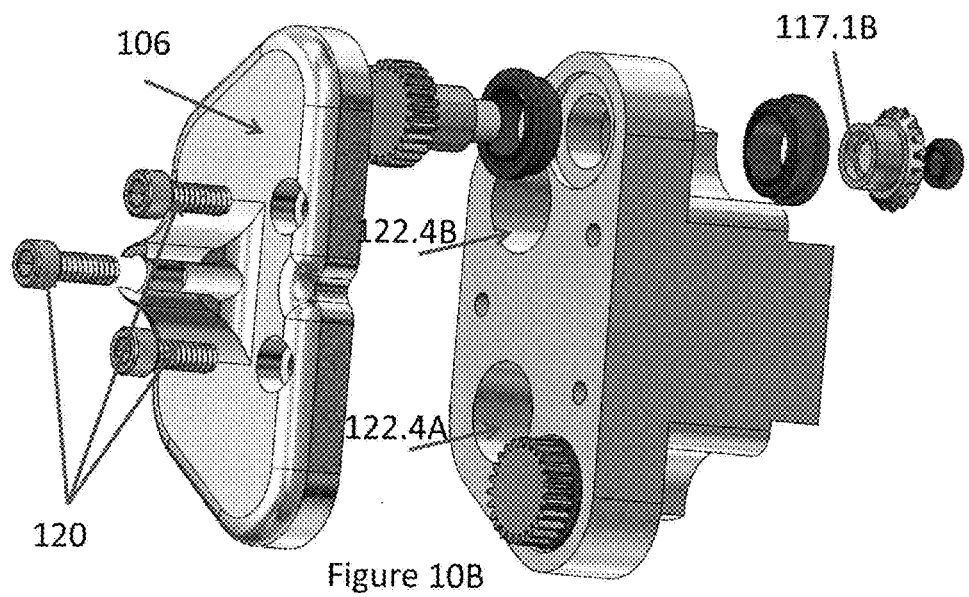
FIG. 10B is an perspective exploded view of the body segments of a robotic device, according to the embodiment of FIG. 10A.

FIGS. 10A and 10B depict the fifth 105 and sixth 106 segments, both of which are also components of the second housing 100.2 discussed above and depicted in FIGS. 5A and 5B. It should be noted that FIGS. 10A and 10B depict the back side of these segments, while the other figures discussed herein relating to the other segments generally depict the front side. In one implementation, the sixth segment 106 is an end cap segment that couples to the fifth segment 105. The fifth segment, 105, like the fourth 104, has right and left lumens 119.1A, 119.1B defined in the fifth segment 105 that are configured to receive the right 119.3A and left distal spur shafts 119.3B, both of which are part of the drive trains that operably couple the right 122A and left 122B distal motors to the right 127A and left 127B shoulder subassemblies that constitute the right 300.1A and left 300.1B shoulders of the device. In addition, the segment 105 also has right and left fifth segment lumens 122.4A, 122.4B configured to receive the right 122A and left 122B distal motors as best shown in FIGS. 12A and 12B and discussed below.

While the drive train that includes the first left distal spur shaft 119.3B will be discussed in detail in this paragraph, it is understood that the drive train that includes the first right distal spur shaft 119.3A has the same components that are coupled and function in the same manner The first left distal spur shaft 119.3B is configured to be disposed through the left fifth segment lumen 119.1B. It has a left distal driven gear 119.2B at one end and is coupled to a left distal bevel gear 117B at the other. In addition, a fourth ball bearing 116B is positioned within an opening or recess in the left distal bevel gear 117B and is contacted only on its outer race by the inner wall of the opening in the left distal bevel gear 117B. Further, the fifth ball bearing 118.1B is positioned over/on the bore of left distal bevel gear 117B and within the left fifth segment lumen 119.1B, while the fifth ball bearing 118.2B is positioned on/over spur the left distal gear shaft 119B and within the left fifth segment lumen 119.1B at the opposite end of the fifth segment lumen 119.1B from fifth ball bearing 118.1B. According to one embodiment, the left distal bevel gear 117B is coupled to the first left distal spur shaft 119.3B via a threaded coupling (not shown). That is, the left distal bevel gear 117B has a left distal bevel gear lumen 117.1B as best shown in FIG. 10B that contains internal threads (not shown) while the first left distal spur shaft 119.3B has external threads (not shown) defined on an outer surface at the end of the first left distal spur shaft 119.3B that comes into contact with left distal bevel gear 117B. In one implementation, a thread locker is used to permanently affix the left distal bevel gear 117B to the first left distal spur shaft 119.3B. According to one particular exemplary embodiment, the thread locker can be Loctite, as described above. In one embodiment, the act of coupling the internal threads in the left distal bevel gear lumen 117.1B with the external threads on the outer surface of the first left distal spur shaft 119.3B preloads the fifth and sixth ball bearings 118.1B, 118.2B.

Figure 11A:
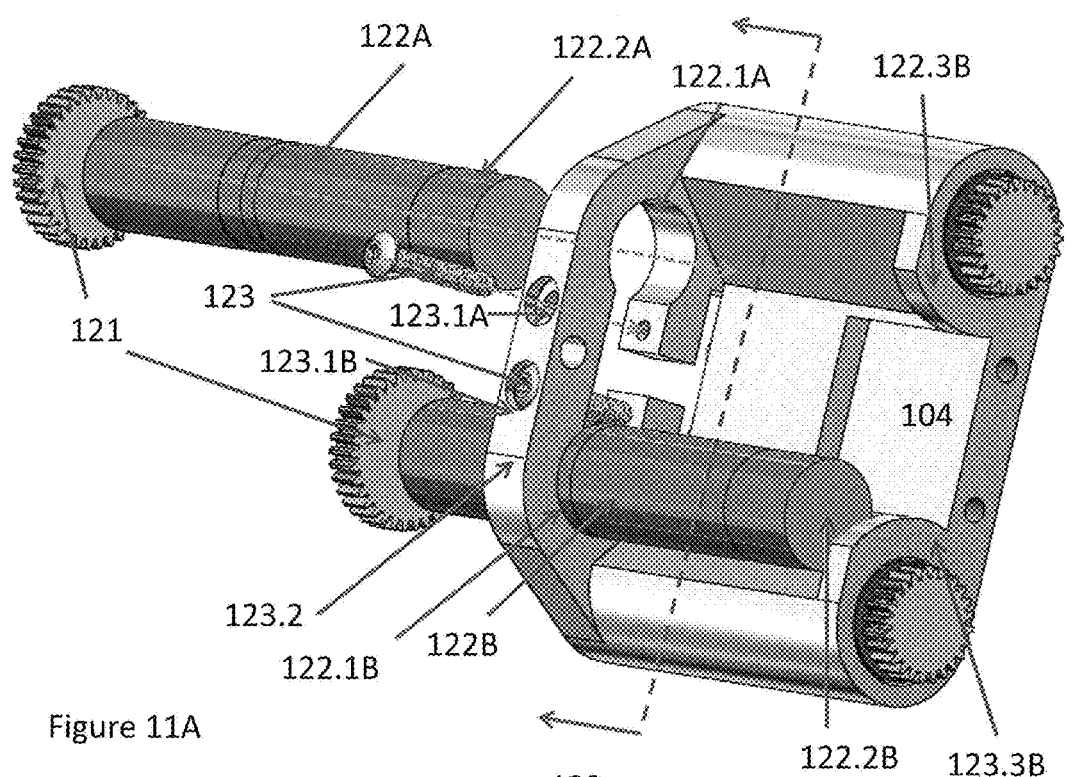
FIG. 11A is an perspective exploded view of a body segment of a robotic device, according to another embodiment.
Figure 11B:
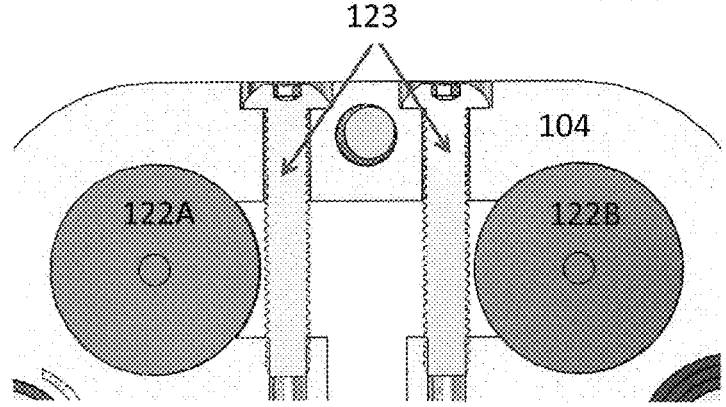
FIG. 11B is an endlong sectional view of a body segment of a robotic device, according to the embodiment of FIG. 11A.

FIGS. 11A and 11B depict the fourth segment 104 and, more specifically, the positioning of the right distal motor 122A and left distal motor 122B in the fourth segment holes 122.1A, 122.1B. The right distal motor 122A and left distal motor 122B, according to one embodiment, are 10 mm motors that are similar or identical to the right and left proximal motors 109A, 109B discussed above. Alternatively, any known motors can be used. Each of the right distal motor 122A and left distal motor 122B have a second right distal spur gear 121A and second left distal spur gear 121B, respectively. In one embodiment, each second distal spur gear 121A, 121B is coupled to the distal motor 122A, 122B with "D" geometry as described above and, in some embodiments, adhesive such as JB-Weld. As shown in FIGS. 11A, the right distal motor 122A and left distal motor 122B are positioned in the right and left fourth segment holes 122.1A, 122.1B. In one implementation, the right distal motor 122A and left distal motor 122B are positioned correctly when the right and left distal motor ends 122.2A, 122.2B contact or are substantially adjacent to the right and left distal stop tabs 122.3A, 122.3B. When the right distal motor 122A and left distal motor 122B are positioned as desired, the threaded members 123 are inserted in the right and left threaded member holes 123.1A, 123.1B and tightened, thereby urging the fourth segment crossbar 123.2 downward and thereby constraining the right distal motor 122A and left distal motor 122B rotationally and translationally within the fourth segment holes 122.1A, 122.1B.

Figure 12A:
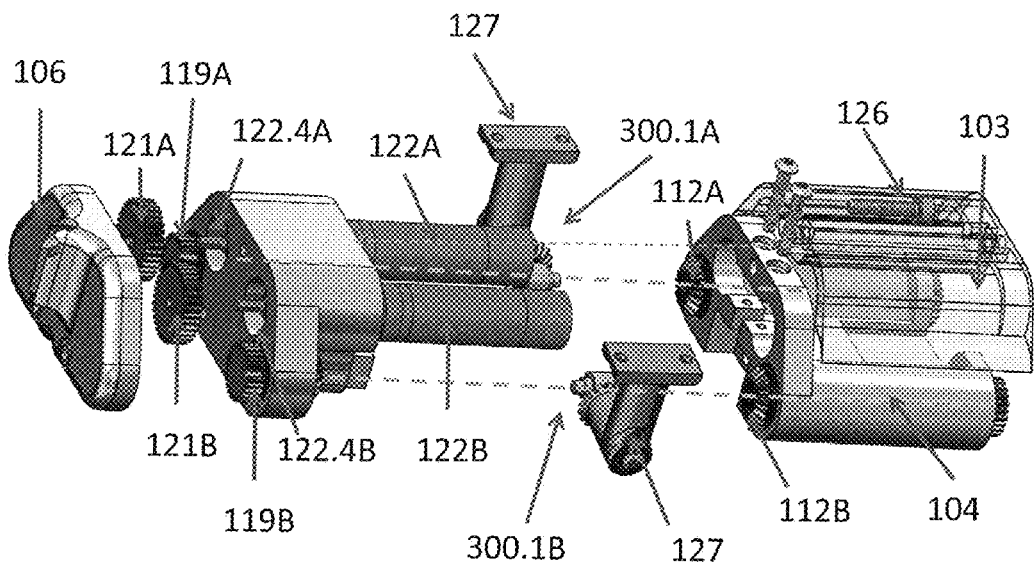
FIG. 12A is an perspective exploded view of the body segments of a robotic device, according to another embodiment.
Figure 12B:
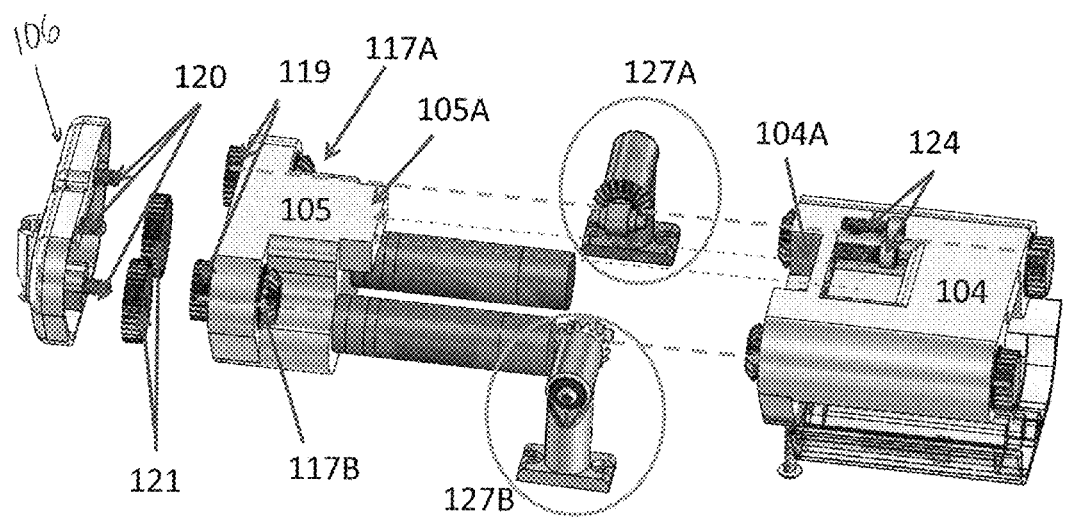
FIG. 12B is an opposite perspective exploded view of the body segments of a robotic device, according to the embodiment of FIG. 12A.

FIGS. 12A and 12B depict the fourth, fifth and sixth segments 104, 105, 106 of the second housing 100.2 and how they are coupled together to form the second housing 100.2. As will be explained in detail below, the fourth, fifth and sixth segments 104, 105, 106 couple together into a second housing 100.2 that forms the right 300.1A and left shoulders 300.1B of the device. The right distal motor 122A and left distal motor 122B are positioned through the fifth segment lumens 122.4A, 122.4B such that the second distal spur gears 121A, 121B that are coupled to the right distal motor 122A and left distal motor 122B are positioned against the fifth segment 105 and between the fifth 105 and sixth segments 106. The second distal spur gears 121A, 121B transmit the rotational motion from the right distal motor 122A and left distal motor 122B, respectively to the distal spur shafts 119.3A, 119.3B, which are positioned such that they are coupled to the second distal spur gears 121A, 121B. As described in detail with respect to FIGS. 10A and 10B, the first distal spur shafts 119.3A, 119.3B are coupled to the second right bevel gear, 117B so that the motion is also transferred through the second right bevel gear, 117B.

When the fourth, fifth and sixth segments 104, 105, 106 are coupled together to form the second housing 100.2, in one embodiment, a fifth segment projection 105A on the back of the fifth segment 105 is positioned in and mates with a fourth segment notch 104A in the back of the fourth segment 104, as best shown in FIG. 12B. Further threaded members are then threaded through holes in the fourth segment (not shown) and into the projection 105A, thereby further securing the fourth and fifth segments 104,105. This mated coupling of the fifth segment projection 105A and fourth segment notch 104A can, in one implementation, secure the fourth and fifth segments 104, 105 to each other such that neither component is rotational in relation to the other, while the threaded members secure the segments translationally.

In one implementation best shown in FIG. 12A, the third segment 103 can serve as a protective cover that can be coupled or mated with the front portion of the fourth segment 104 and retained with a threaded member 126. In these embodiments, the third segment 103 can help to protect the motors and electronics in the second housing 100.2. In addition, a gearcap cover segment 106 can be coupled or mated with the bottom portion of the fourth segment 104 and retained with threaded members 120. The cover segment 106 can help to cover and protects the various gears 119A, 119B, 121A, 121B contained within the fourth segment 104. The coupling of the fourth 104 and fifth 105 segments also results in the positioning of the second right bevel gear 117A in relation to the first right bevel gear, 112B such that the second right bevel gear 117A and the first right bevel gear 112A are positioned to couple with the right shoulder subassembly 127A to form the right shoulder 300.1A and the corresponding left bevel gears 117B, 112B are positioned to couple with the subassembly left shoulder subassembly 127B to form the left shoulder 300.1B. This is depicted and explained in further detail in FIGS. 13A-14C.

FIGS. 13A-13D and 14A-14C depict the shoulder subassembly design, according to one embodiment. The components in these figures are numbered and will be described without reference to whether they are components of the right shoulder (designated with an "A" at the end of the number) or the left shoulder (designated with a "B" at the end of the number). Instead, it is understood that these components are substantially similar on both sides of the device and will be described as such.

The shoulder subassemblies 127A, 127B of the right shoulder 300.1A and left shoulder 300.1B respectively, have output bevel gears 130A, 130B (which couples with the right bevel gears 112A, 117A and left bevel gears 112B, 117B) having a right lumen 130A and left lumen (not pictured) configured to receive the right output shaft 128A and left output shaft. The right output shaft 128A is positioned in the lumen 130A and also has two projections (a first 128A.1, and second 128A.2) that are configured to be positioned in the lumens of the first and second right bevel gears 112A, 117A. In addition, a plurality of ball bearings 111, 116 are positioned over the projections 128A.1, 128A.2 such that the inner race of the bearings 111, 116 contact the projections 128A.1, 128A.2.

A further ball bearing 129A is positioned on/over the right output shaft 128A such that the ball bearing 129 is positioned within the lumen 130A of the right output bevel gear 130A. Yet a further ball bearing 131 is positioned in the opposing side of the right output bevel gear lumen 130A and on/over a threaded member 132. The threaded member 132 is configured to be threaded into the end of the right output shaft 128A after the shaft 128A has been positioned through the lumen 130A of the right output bevel gear 130A, thereby helping to retain the right output bevel gear 130A in position over the right output shaft 128A and coupled with the first and second right bevels gears 112A, 117A. Once the threaded member 132 is positioned in the right output shaft 128A and fully threaded therein, the full right shoulder subassembly 127A is fully secured such that the right output bevel gear 130A is securely coupled to the first and second right bevel gears 112A, 117A.

Figure 13A:
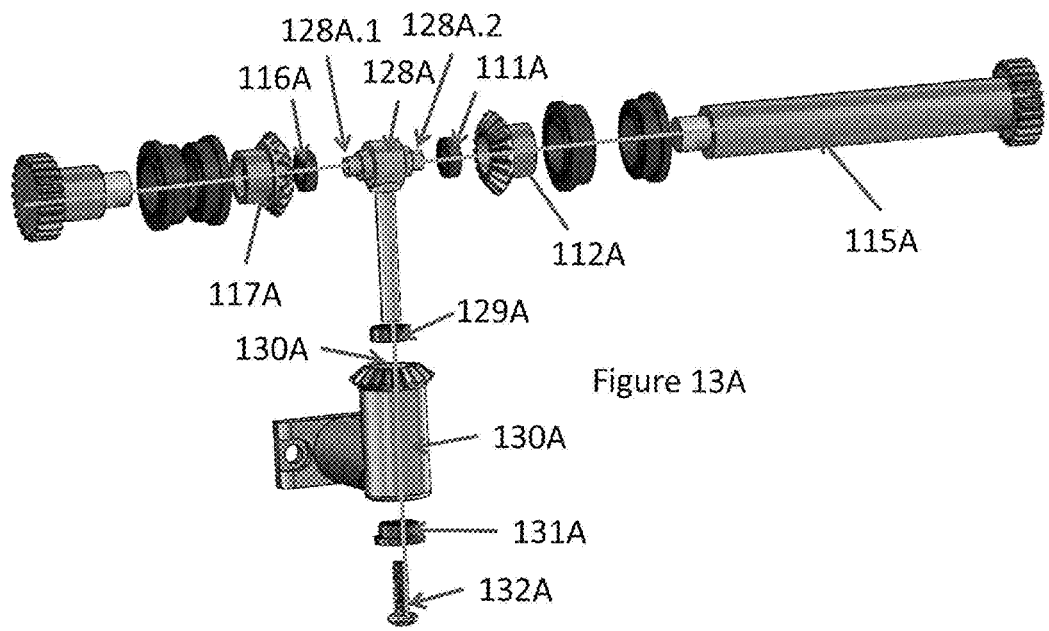
FIG. 13A is an perspective exploded view of the shoulder joint of a robotic device, according to another embodiment.
Figure 13B:
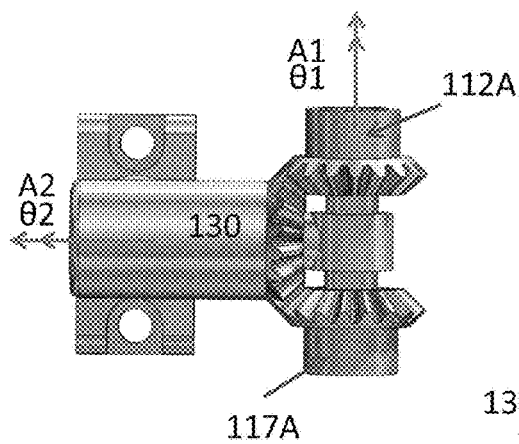
FIG. 13B is a side view of the shoulder joint of a robotic device, according to the embodiment of FIG. 13A.
Figure 13C:
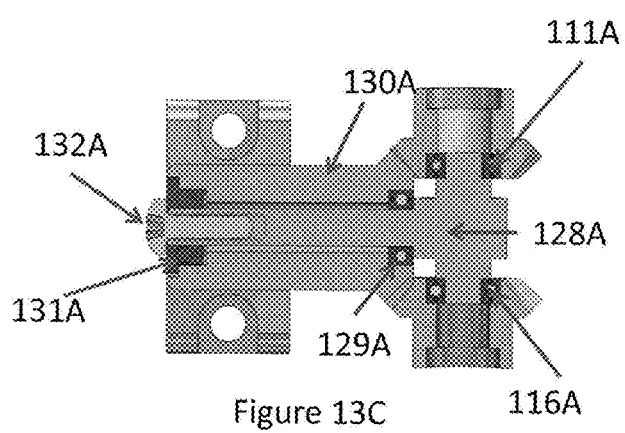
FIG. 13C is a cross sectional view of a shoulder joint of a robotic device, according to the embodiment of FIG. 13A.
Figure 13D:
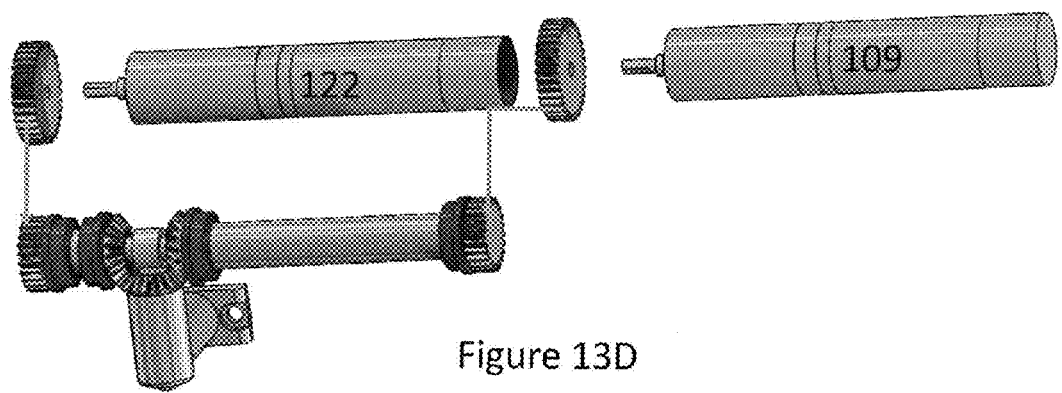
FIG. 13D is an exploded perspective view of a shoulder joint of a robotic device, according to the embodiment of FIG. 13A.
Figure 14A:
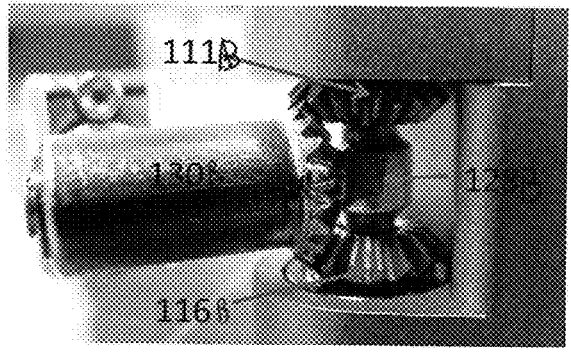
FIG. 14A is a bottom perspective view of the shoulder joint of a robotic device, according to another embodiment.
Figure 14B:
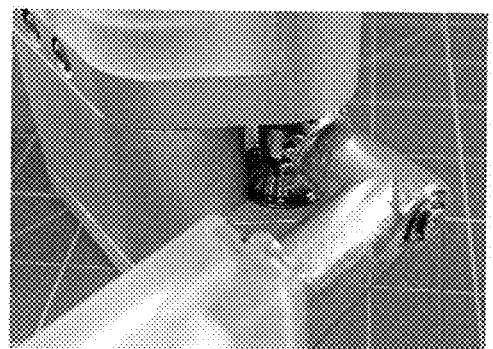
FIG. 14B is a side perspective view of the shoulder joint of a robotic device, according to the embodiment of FIG. 14A.
Figure 14C:
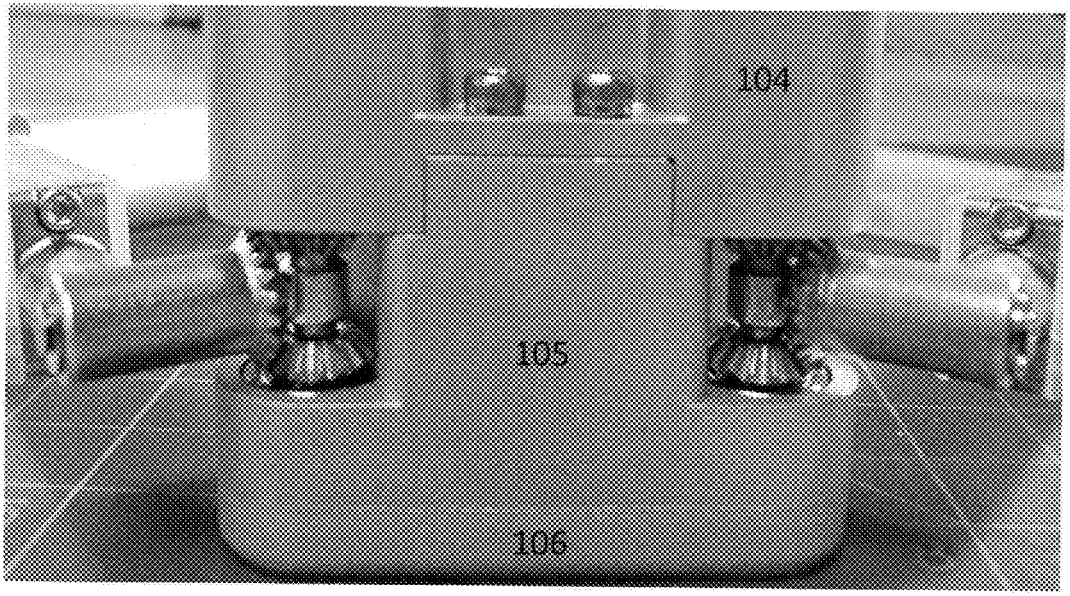
FIG. 14C is a bottom view of the shoulder joints of a robotic device, according to the embodiment of FIG. 14A.
Figure 15A:
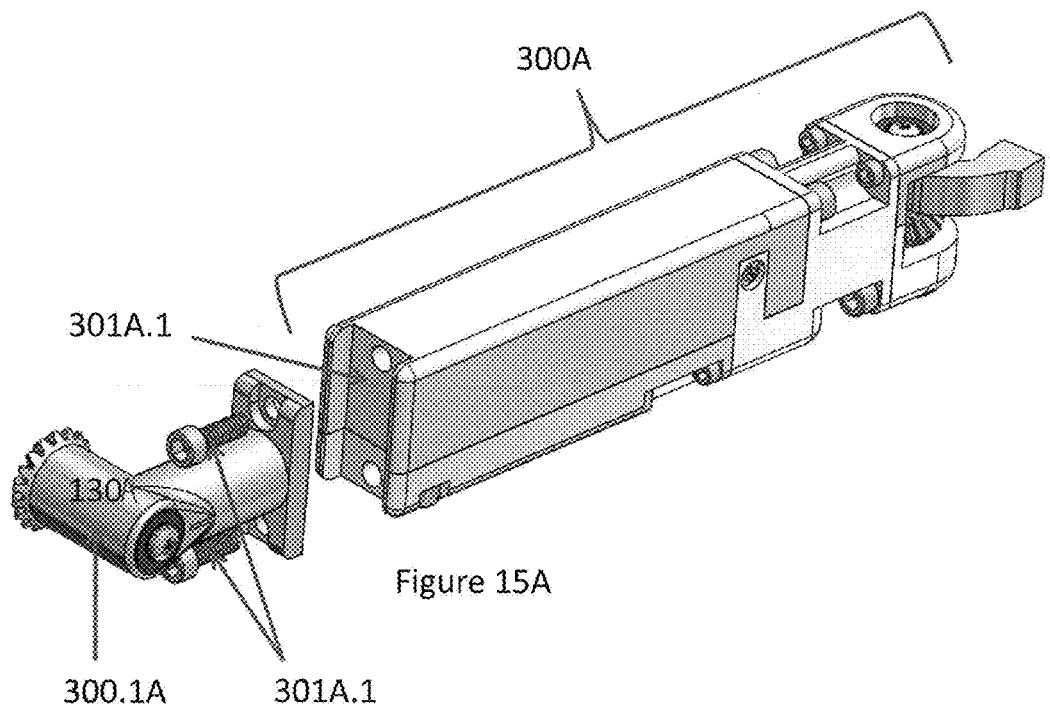
FIG. 15A is a perspective view of the upper arm of a robotic device, according to another embodiment.
Figure 15B:
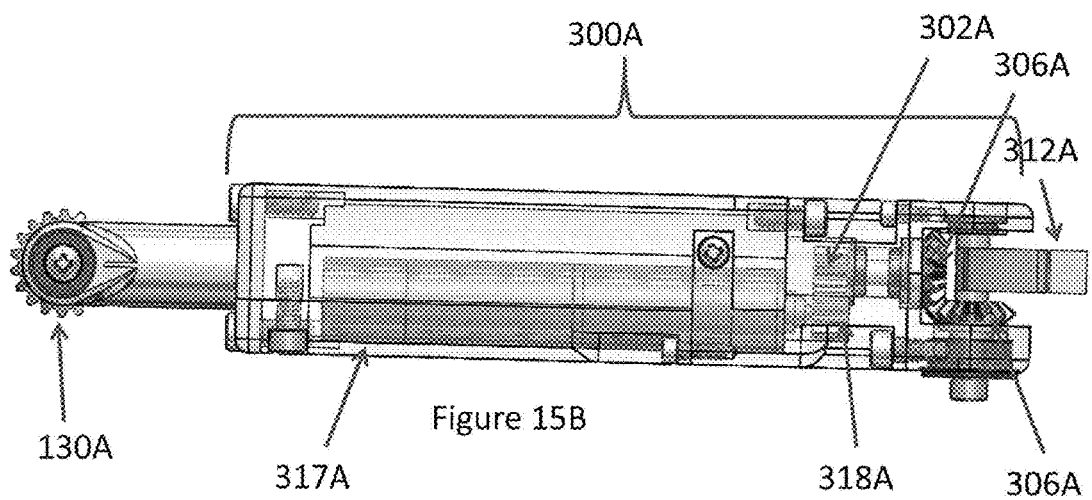
FIG. 15B is a side view of the upper arm of a robotic device, according to the embodiment of FIG. 15A.

In operation, as best shown in FIG. 13B, rotation of the first and second right bevel gears 112A, 117A rotates the right output bevel gear 130, which can cause rotation of the right shoulder subassembly 127A along at least one of two axes—axis A1 or axis A2—depending on the specific rotation and speed of each of the first and second right bevel gears 112A, 117A. For example, if both first and second right bevel gears 112A, 117A are rotated in the same direction at the same speed, the first and second right bevel gears 112A, 117A are essentially operating as if first and second right bevel gears 112A, 117A are a fixed, single unit that cause rotation of the shoulder subassembly 127A around axis Al. In an alternative example, if the first and second right bevel gears 112A, 117A are rotated in opposite directions, the right output bevel gear 130A is rotated around axis A2. It is understood that the first and second right bevel gears 112A, 117A can also work together to achieve any combination of rotation along both axes A1, A2. That is, since the first and second right bevel gears 112A, 117A are driven independently by the distal and proximal motors 122A, 109A, any combination of θ1 and θ2 are achievable around axes A1 and A2. As an example, if both gears 112A, 117A are rotated in the same direction but at different speeds, this will result in a combined rotation of the subassembly around both the A1 axis and the A2 axis, as would be clear to one of skill in the art FIGS. 15A and 15B depict a right upper arm (or first link) 300A that is coupled to the device body 100 at right shoulder 300.1A (as also shown in FIGS. 1 and 2). While the following figures and discussion focus on the right upper arm 300A, it is understood that the left upper arm 300B can have the same or similar components and thus that the discussion is relevant for the left upper arm 300B as well. As shown in FIGS. 15A and 15B, the upper arm 300A is coupled to the output bevel gear 130A with two threaded screws 301A.1. In addition, according to certain embodiments, the upper arm 300A has a notch 301.1A defined in the proximal end of the arm 300A into which the output bevel gear 130A is positioned, thereby providing additional mating geometry that further secures the upper arm 300A and the output bevel gear 130A.

As best shown in FIG. 15B, the upper arm 300A has an upper arm motor 317A that actuates the movement of the forearm 200A at the elbow joint 200.1A of the arm A. That is, the motor 317 is coupled to an upper arm spur gear 318A, which is coupled to an upper arm driven gear 302A. The driven gear 302A is coupled to a first right upper arm bevel gear 306A, which is coupled to a second right upper arm bevel gear 313A. The second right upper arm bevel gear 313A is coupled to an upper arm output upper arm shaft 312AA, which is coupled to the right forearm 200A. Each of these components and how they are coupled to each other will now be described in further detail below.

Figure 16A:
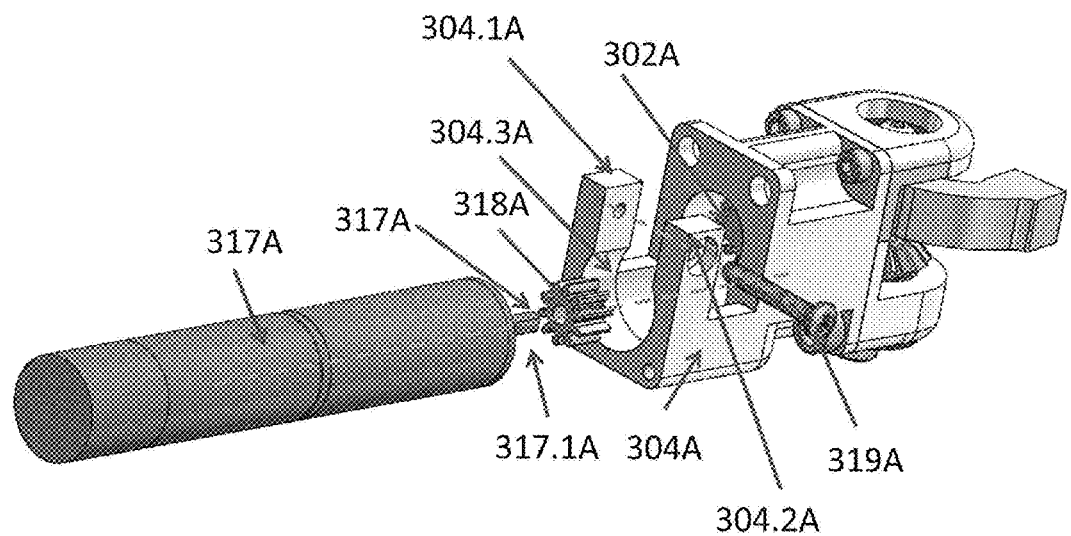
FIG. 16A is an exploded perspective view of the motor and drive train of a robotic device, according to another embodiment.
Figure 16B:
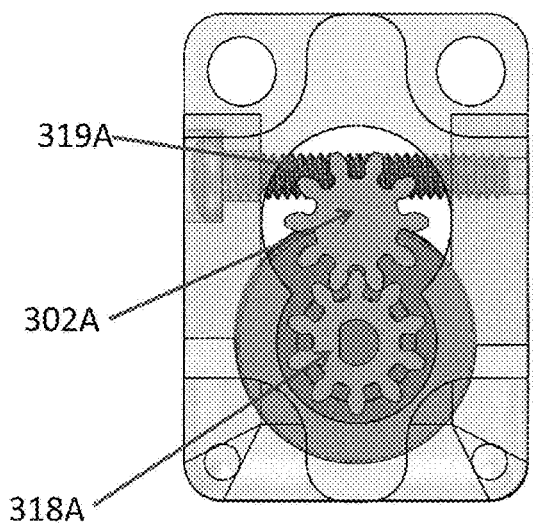
FIG. 16B is a side view of the motor and drive train of a robotic device, according to the embodiment of FIG. 16A.

FIGS. 16A and 16B depict the right upper arm motor 317A and the drive train coupled to the motor 317A in the upper arm 300A. In this embodiment, the motor 317A is an 8 mm motor that is positioned in the upper arm 300A. The upper arm spur gear 318A is coupled to the upper arm motor output shaft 317A and rotationally secured via a "D" geometry 317.1A. According to one embodiment, the upper arm spur gear 318A is further secured with JB-Weld. The upper arm 300A also has a housing 304A positioned in the arm 300A that is configured to house or support the drive train that is coupled to the upper arm motor 317A. The housing 304 has a hole 304.3A defined by two arms 304.1A, 304.2A that is configured to receive the motor 317A. When the motor 317A and upper arm spur gear 318A have positioned correctly within the hole 304.3A such that the upper arm spur gear 318A is coupled to the upper arm spur shaft gear 302A, a screw 319A can be positioned through holes in both arms 304.1A, 304.2A and tightened, thereby urging the arms 304.1A, 304.2A together and securing the upper arm motor 317A both rotationally and translationally within the hole 304.3A. In one alternative, an adhesive such as epoxy can be added help to further restrict unwanted movement of the upper arm motor 317A in relation to the upper arm housing 304A. This securing of the motor 317A in the upper arm housing 304A ensures proper coupling of upper arm spur gear 318A with the upper arm spur shaft gear 302A.

Figure 17A:
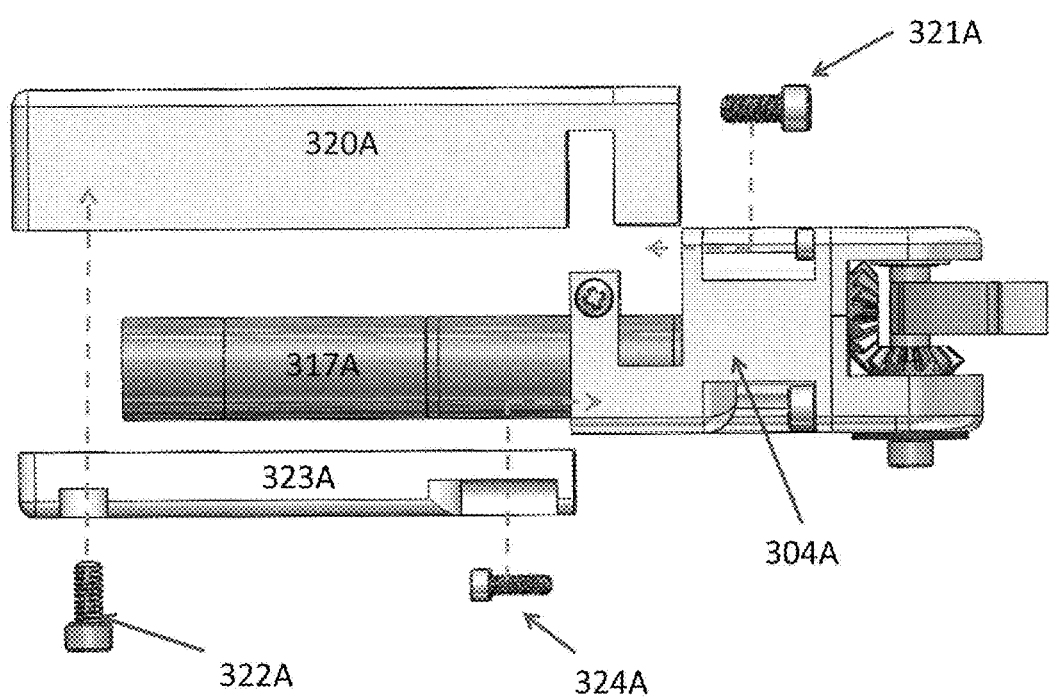
FIG. 17A is an exploded side view of the housing segments of a robotic device, according to another embodiment.
Figure 17B:
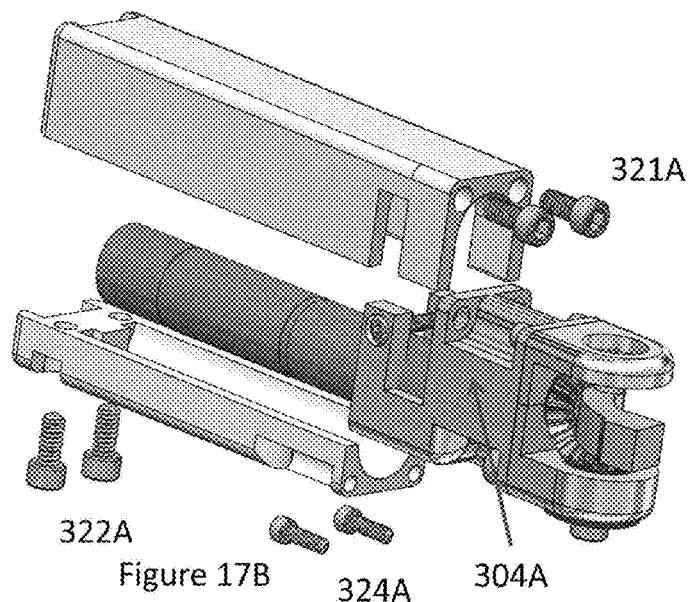
FIG. 17B is an exploded perspective view of the housing segments of a robotic device, according to the embodiment of FIG. 17A.

FIGS. 17A and 17B depict the first 320A and second 232A segments (or "shells") that couple together to create the housing around the upper arm motor 317A. The first shell 320A is positioned above the upper arm motor 317A and the second shell 323A is positioned beneath the motor 317A. The two shells 320A, 323A are coupled together with screws 322A that are positioned through the second shell 323A and into the first shell 320A. In addition, the two shells 320A, 323A are also coupled to the upper arm housing 304A, with the first shell 320A being coupled to the upper arm housing 304A with screws 321A and the second shell 323A being coupled to the upper arm housing 304A with further screws 324A.

Figure 18A:
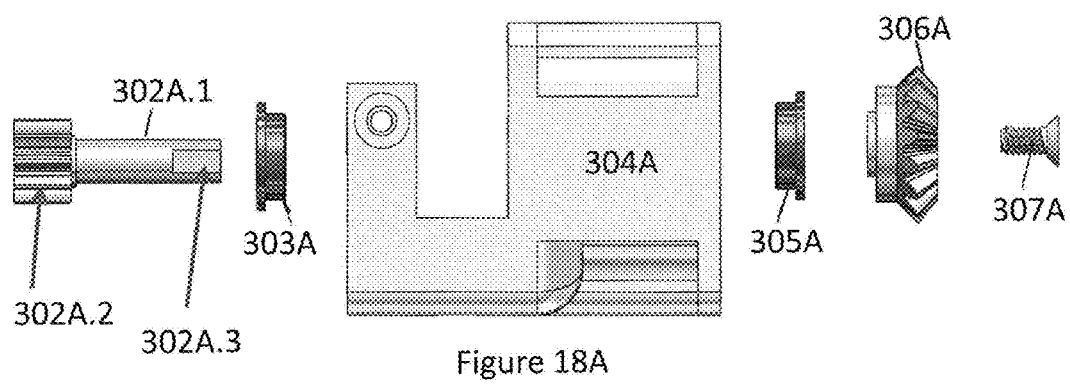
FIG. 18A is an exploded side view of the housing and spur shaft of a robotic device, according to another embodiment.
Figure 18B:
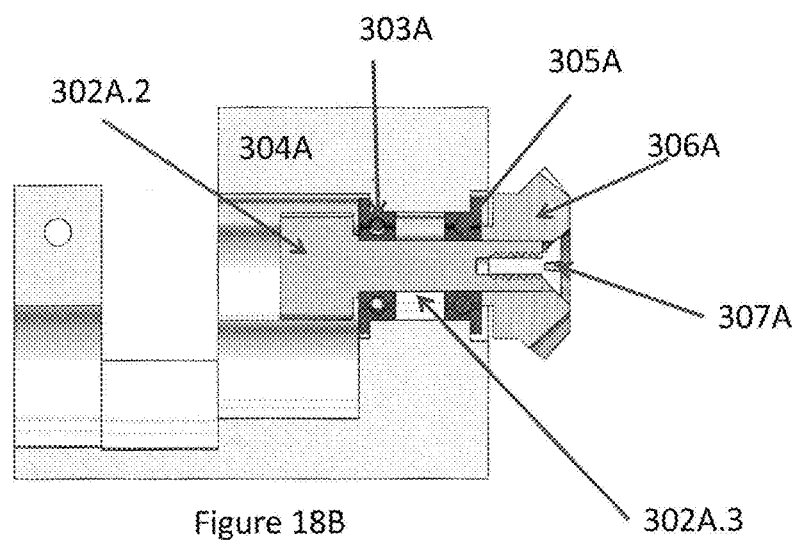
FIG. 18B is an assembled side cross-sectional view of the housing and spur shaft of a robotic device, according to the embodiment of FIG. 18A.

FIGS. 18A and 18B depict the right upper arm housing 304A and further depict the right upper arm spur shaft 302A.1 positioned in the housing 304A. The right upper arm spur shaft 302A has a right upper arm spur gear 302A.2 at one end of the spur shaft 302A.1 as best shown in FIG. 18A. The spur shaft 302A.1 is positioned in an upper arm housing lumen 304A.1 defined in the housing 304A. There are two ball bearings 303, 305 positioned on/over the spur shaft 302A.1 and further positioned at the openings of the upper arm housing lumen 304A.1. A first upper arm bearing 303 is positioned on/over the spur shaft 302A.1 so that only its inner race is contacting the shaft 302A.1. A second upper arm bearing 305A is positioned on/over spur shaft 302A.1 in the same manner The first right upper arm bevel gear 306A is coupled to the upper arm spur shaft 302A.1 at the end opposite the spur shaft gear 302A.2. The upper arm bevel gear 306A is secured to the spur shaft 302A.1 with "D" geometry 302A.3. In a further embodiment, the first right upper arm bevel gear 306A can also be further secured using adhesive such as JB-Weld. A screw 307A is positioned through the first right upper arm bevel gear 306A and into the spur shaft 302A.1 such that when the screw 307A is fully threaded into the spur shaft 302A.1, the screw 307A translationally secures first right upper arm bevel gear 306A and also preloads the first 303 and second 305 upper arm bearings.

Figure 19A:
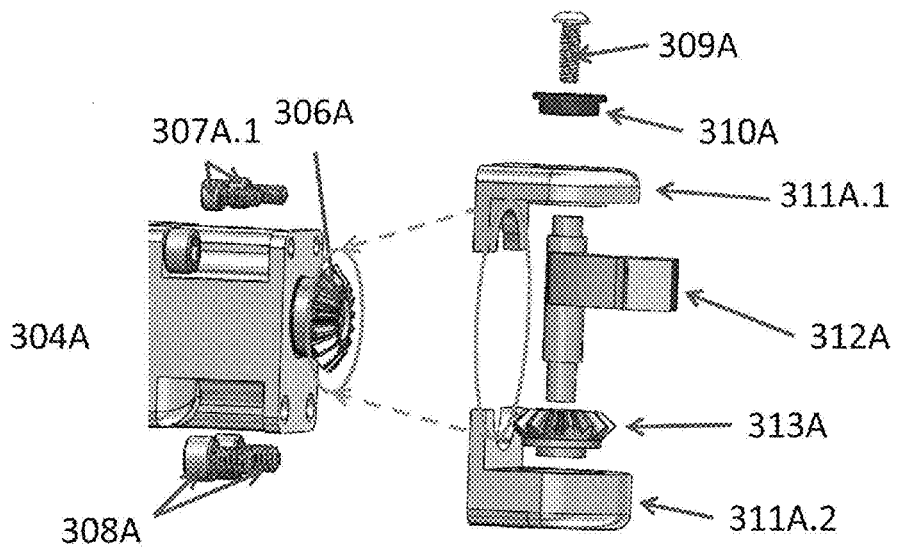
FIG. 19A is an exploded side perspective view of the shaft housing and housing of a robotic device, according to another embodiment.
Figure 19B:
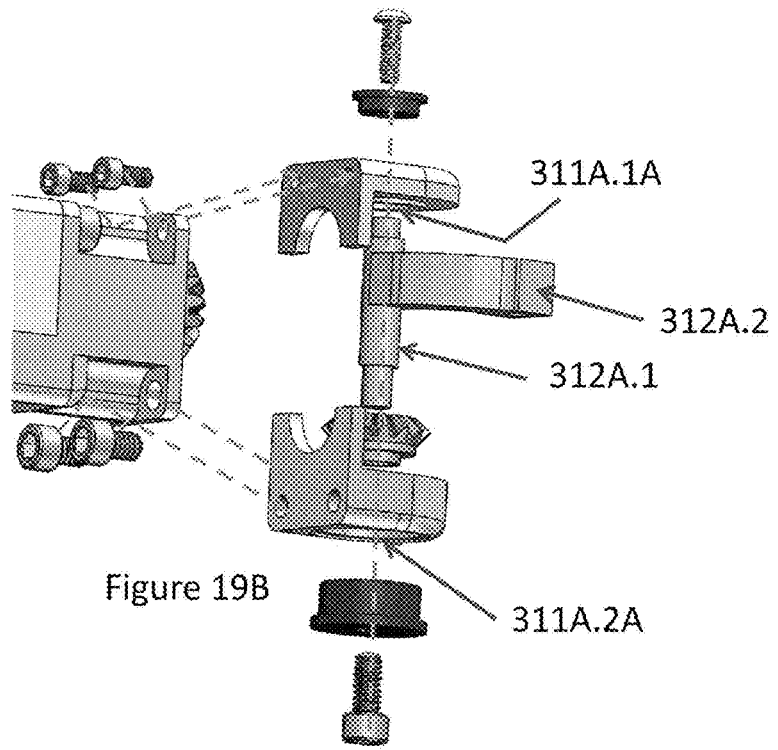
FIG. 19B is an opposite exploded side perspective view of the shaft housing and housing a robotic device, according to the embodiment of FIG. 19A.
Figure 19C:
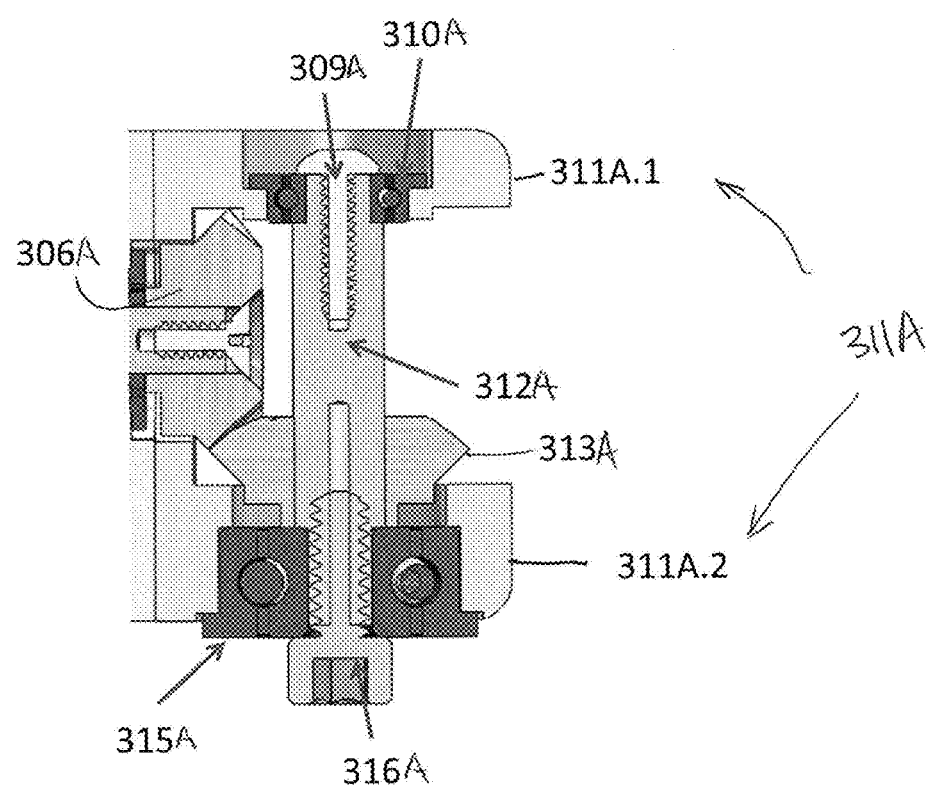
FIG. 19C is a cross-sectional view of the shaft housing and housing a robotic device, according to the embodiment of FIG. 19A.
Figure 20A:
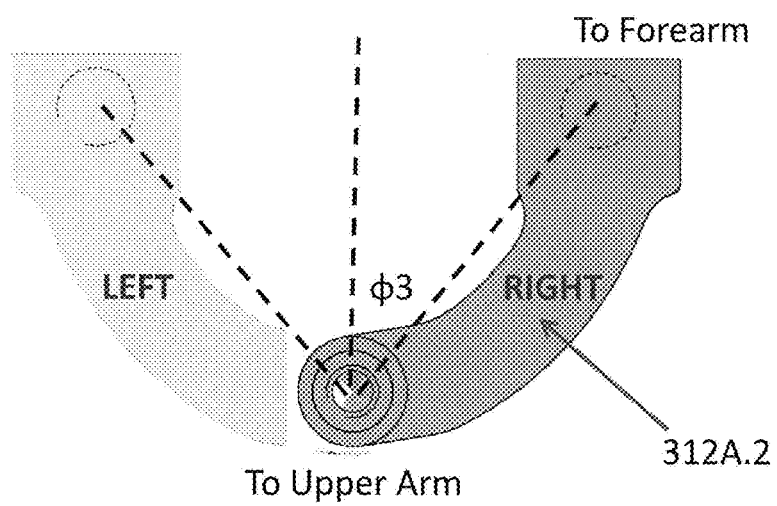
FIG. 20A is a side view of the shaft of a robotic device, according to another embodiment.
Figure 20B:
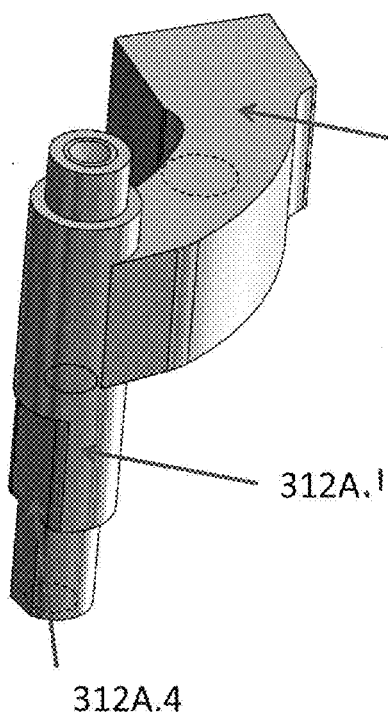
FIG. 20B is a perspective view of the shaft of a robotic device, according to the embodiment of FIG. 20A.
Figure 20C:
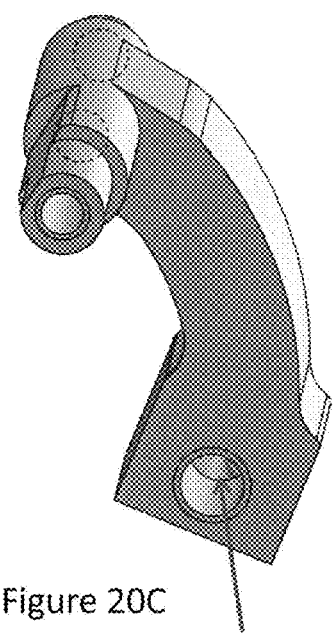
FIG. 20C is another perspective view of the shaft of a robotic device, according to the embodiment of FIG. 20A.

FIGS. 19A, 19B, and 19C depict the upper arm shaft housing 311A coupled to the upper arm housing 304. The upper arm shaft housing 311A is made up of an upper shaft housing arm 311A.1 and a lower shaft housing arm 311A.2, both of which are coupled to the upper arm housing 304A. The upper shaft housing arm 311A.1 is coupled to the housing 304A via a first pair of screws 307A.1, while the lower shaft housing arm 311A.2 is coupled via a second pair of screws 308A.1. As best shown in FIG. 19B, each of the shaft housing arms 311A.1, 311A.2 has a hole 311A.1A, 311A.2A. The upper arm shaft 312AA, as best shown in FIGS. 20A-20C, has a vertical shaft component 312A.1 and an appendage 312A.2 coupled to the vertical shaft component 312A.1. The upper arm shaft 312AA is oriented in the assembled shaft housing 311A such that an upper portion of the vertical shaft component 312A.1 is positioned in the hole 311A.1A and a lower portion of the vertical shaft component 312A.1 is positioned in the hole 311A.2A. In addition, a vertical shaft bevel gear 313A is positioned over the vertical shaft component 312A.1 and above the lower shaft housing arm 311A.2 such that the vertical shaft bevel gear 313A is coupled to the first right upper arm bevel gear 306A when all components are properly positioned as best shown in FIG. 19C. The vertical shaft bevel gear 313A is coupled to the vertical shaft component 312A.1 rotationally by a "D" geometry 312A.4 as best shown in FIG. 20B. In a further implementation, the vertical shaft bevel gear 313A can be further secured using JB-Weld. The vertical shaft component 312A.1 also has two ball bearings: a first vertical shaft ball bearing 315A is positioned over the vertical shaft component 312A.1 and through hole 311A.2A so that it is in contact with the vertical shaft bevel gear 313A, while the second vertical shaft ball bearing 310A is positioned in the hole 311A.1A. A screw 316 is positioned through the first ball bearing 315A and hole 311A.2A and threaded into the bottom of the vertical shaft component 312A.1, thereby helping to secure the upper arm shaft 312AA in the assemble shaft housing 311A and the first ball bearing 315A in the hole 311A.2A. A second screw 309A is threaded into the top of the vertical shaft component 312A.1 to secure and preload the second ball bearing 310.

FIGS. 20A, 20B, and 20C depict upper arm shaft 312A, according to one embodiment. The upper arm shaft 312A has an appendage 312A.2 that is configured to be coupled to the forearm 300A. In addition, the upper arm shaft 312A is rotatable in relation to the upper arm 300A as a result of the plurality of vertical shaft ball bearings, 310A and 315A, as best depicted and described above in relation to FIGS. 19A-C. As such, in operation, the upper arm shaft 312A is rotatable by the right upper arm motor 317AA in the upper arm 300A as described above via the drive train that couples the right upper arm motor 317A to the vertical shaft bevel gear 313A, which in turn is coupled to the upper arm shaft 312A. In one embodiment, the appendage 312A.2 can be rotated around vertical upper arm shaft 312AA with a rotational radius or angle of φ3 as shown in FIG. 20A. In one specific implementation, the angle is 50 degrees. In accordance with one embodiment, the appendage 312A.2 is configured to be coupleable to a forearm 300A via the configuration or geometry of the appendage 312A.2 and the hole 312A.5 formed underneath the appendage 312A.2.

It is understood that any known forearm component can be coupled to either upper arm 300A, 300B. According to one embodiment, the forearm coupled to the upper arm 300A, 300B is the exemplary right forearm 410, which could apply equally to a right 410A or left 410B forearm, depicted in FIGS. 21A-21D. In this exemplary embodiment, the forearm has a cylindrical body or housing 412 and an end effector 414. As shown in FIGS. 21G and 21H, the housing 412 is made up of two separate forearm housing components 412.1, 412.2 that are coupled together with three bolts (or threaded members) 472. The three bolts 472 pass through housing component 412.1 and into threaded holes in the housing component 412.2. Alternatively, the two forearm housing components 412.1, 412.2 can be coupled together by any known coupling mechanism or method.

In this embodiment, the end effector 414 is a grasper, but it is understood that any known end effector can be coupled to and used with this forearm 410. The depicted embodiment can also have a circular valley 474 defined in the distal end of the forearm housing 412. This valley 474 can be used to retain an elastic band or other similar attachment mechanism for use in attaching a protective plastic bag or other protective container intended to be positioned around the forearm 410 and/or the entire device arm and/or the entire device to maintain a cleaner robot.

Figure 21A:
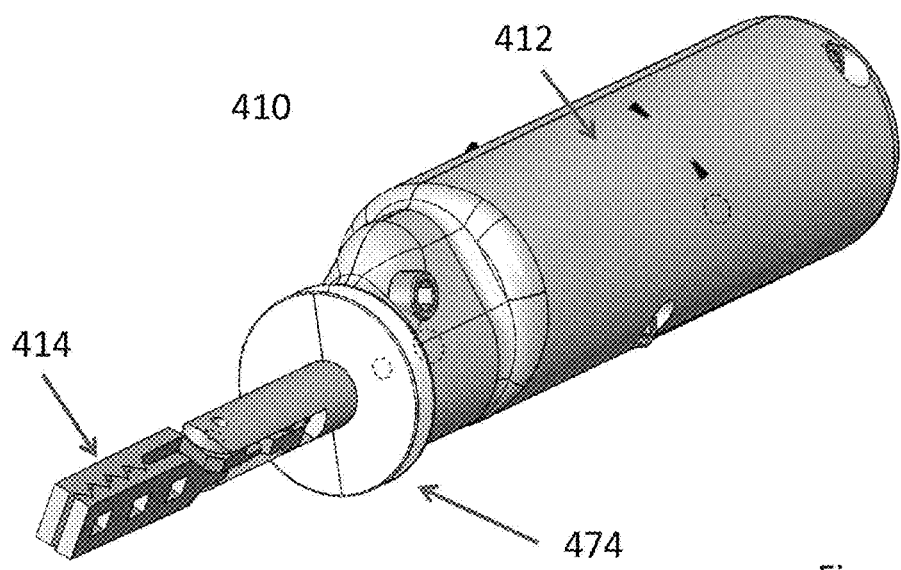
FIG. 21A is a perspective view of the forearm of a robotic device, according to another embodiment.
Figures 21B, 21C, 21D:
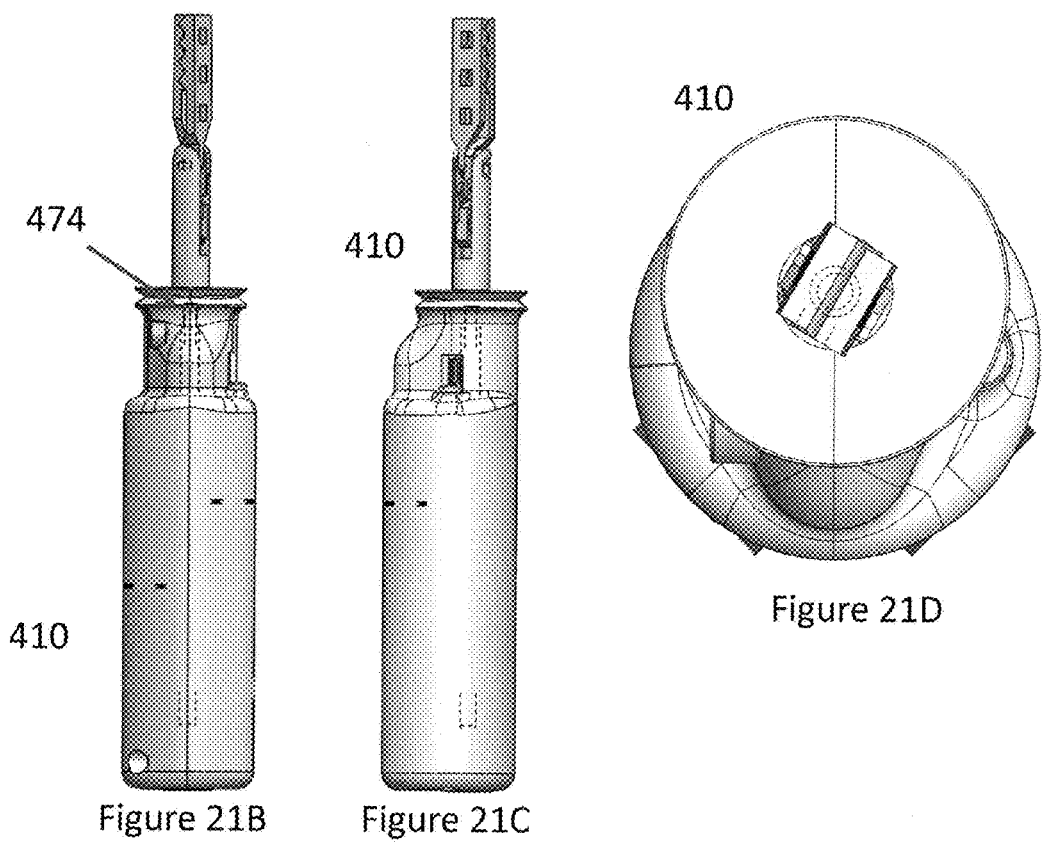
FIG. 21B is a side view of the forearm of a robotic device, according to the embodiment of FIG. 21A.
FIG. 21C is another side view of the forearm of a robotic device, according to the embodiment of FIG. 21A.
FIG. 21D is an end view of the forearm of a robotic device, according to the embodiment of FIG. 21A.
Figure 21E:
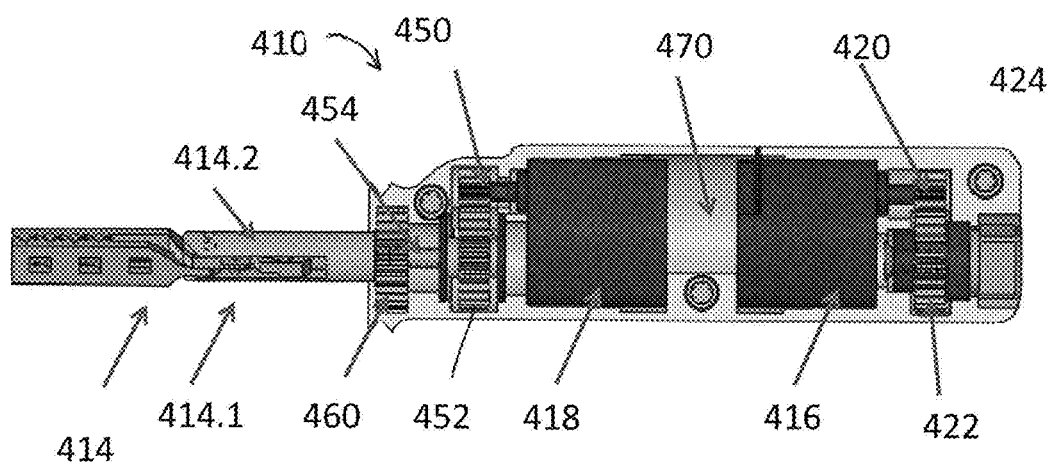
FIG. 21E is a cross sectional side view of the forearm of a robotic device, according to the embodiment of FIG. 21A.
Figure 21F:
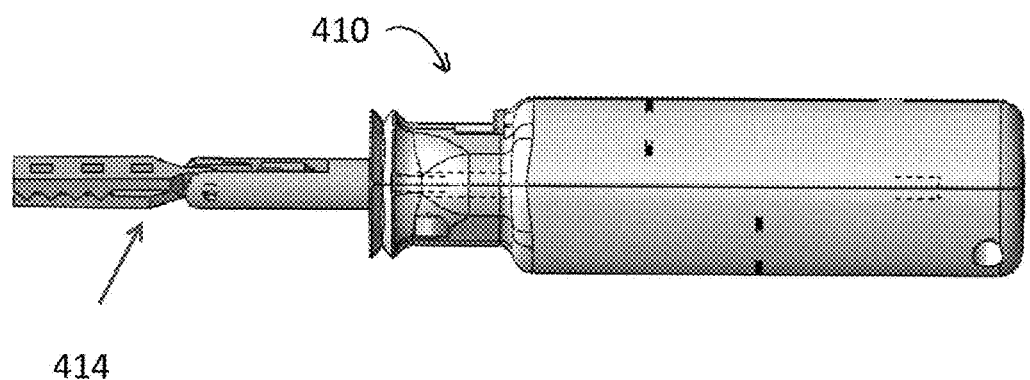
FIG. 21F is a side view of the forearm of a robotic device, according to the embodiment of FIG. 21A.
Figure 21G:
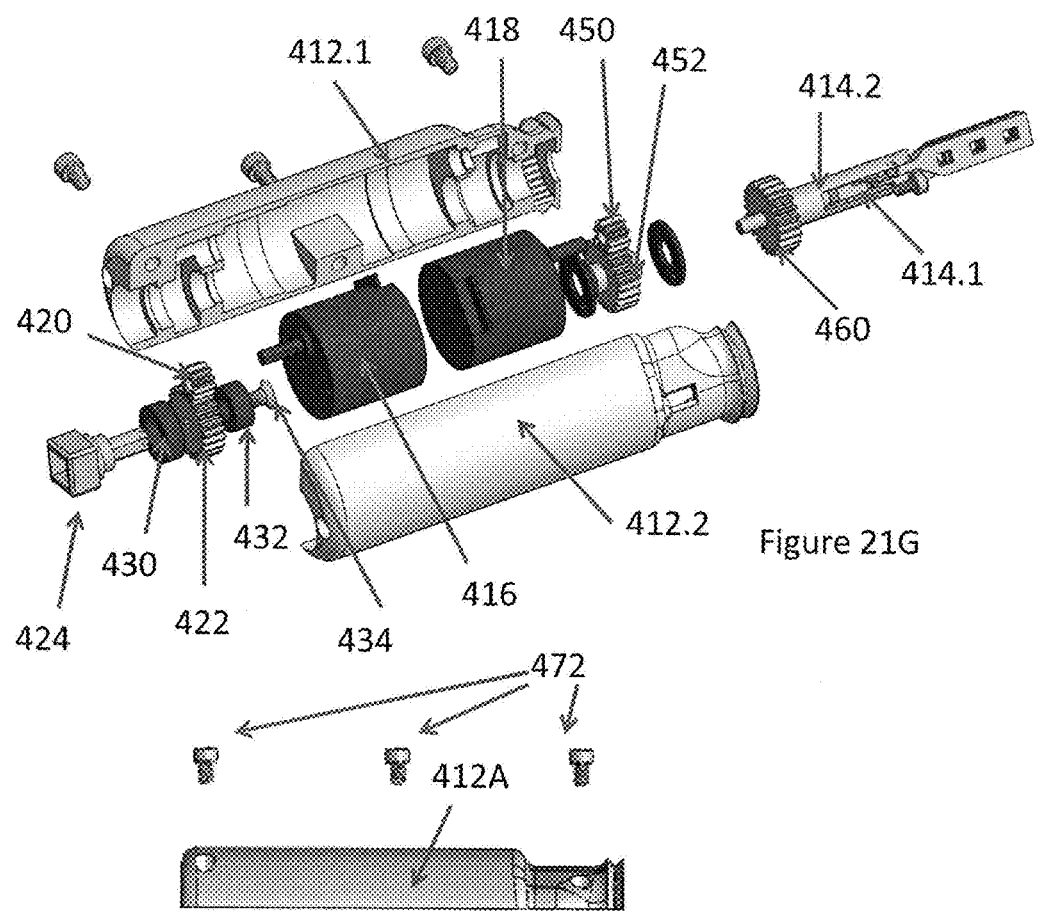
FIG. 21G is an exploded perspective view of the forearm and internal components of a robotic device, according to the embodiment of FIG. 21A.
Figure 21H:
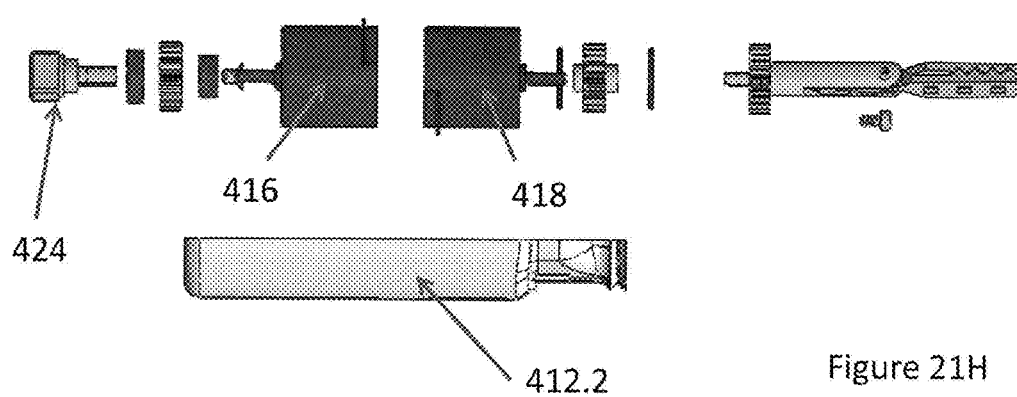
FIG. 21H is a side view of the forearm and internal components of a robotic device, according to the embodiment of FIG. 21A.
Figure 22A:
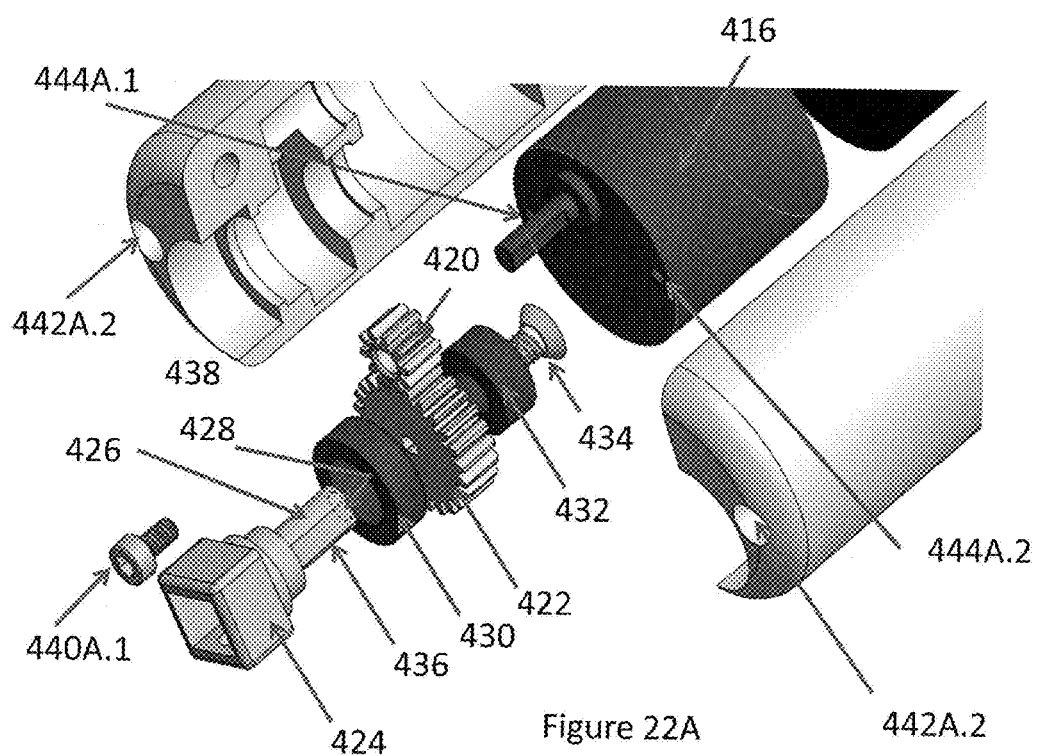
FIG. 22A is an exploded close-up view of the proximal end of the forearm and internal components of a robotic device, according to another embodiment.
Figure 22B:
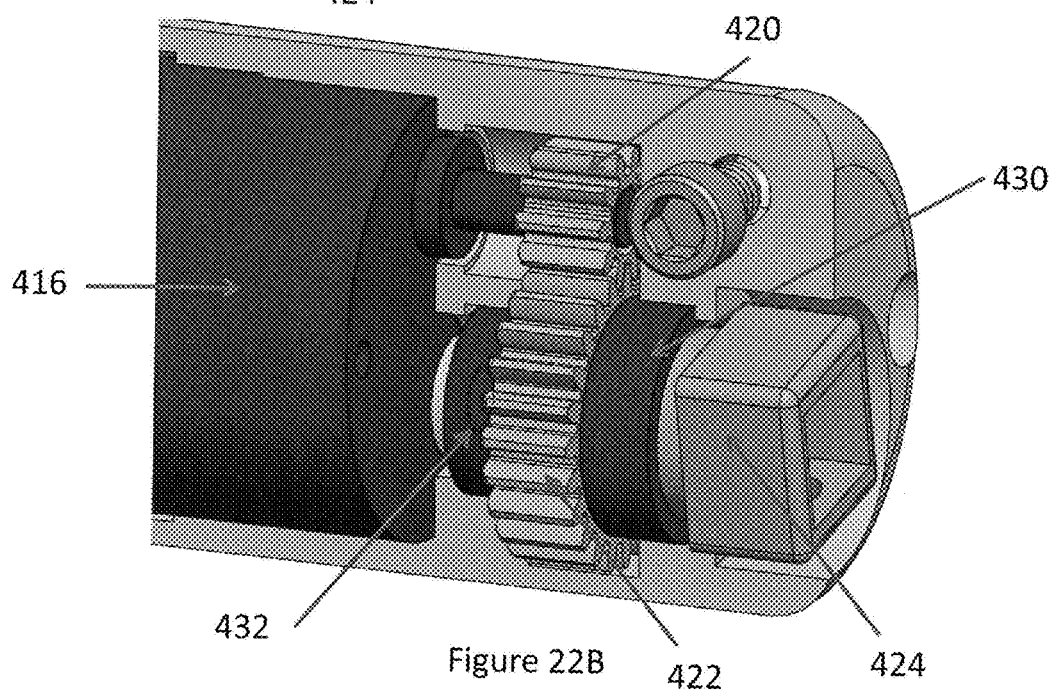
FIG. 22B is a cutaway close-up view of the proximal end of the forearm and internal components of a robotic device, according to the embodiment of FIG. 22A.

As best shown in FIGS. 21E, 21G, and 21H, the forearm 410 has two motors—a rotation motor 416 and an end effector motor 418. The rotation motor 416 is coupled via a forearm rotation motor gear 420 and a forearm rotation motor attachment gear 422 to the forearm attachment component 424, which is configured to be coupleable to an elbow joint, such as either elbow joint 200.1A, 200.1B. The forearm rotation motor attachment gear 422 transmits the rotational drive of the motor from the forearm rotation motor gear 420 to the forearm rotation motor attachment component 424. The attachment component 424, as best shown in FIGS. 22A and 22B, has a forearm rotation motor shaft 426 that defines a forearm rotation motor lumen 428 having a threaded interior wall. Further, the attachment gear 422 and first and second forearm bearings 430, 432 are positioned on/over this shaft 426, thereby operably coupling the attachment gear 422 to the attachment component 424. In one embodiment as shown, the shaft 426 has a D-shaped configuration 436 that mates with the D configuration of the hole 438 defined in the gear 422, thereby rotationally coupling the shaft 426 and gear 422. Alternatively, any configuration that can rotationally couple the two components can be incorporated. The bearing 430 is positioned on the shaft 426 between the attachment component 424 and the attachment gear 422, while the bearing 432 is positioned between the attachment gear 422 and the motor 416. In one embodiment, the bearing 430 is a ball bearing. Alternatively, as with all of the bearings described in this application, these bearings or bushings can be any roller bearings or bushings that can be used to support and couple any rotatable component to a non-rotatable component or housing. The bearings 430, 432, attachment gear 422, and attachment component 424 are secured to each other via a bolt or other type of threaded member 434 that is threaded into the threaded lumen 428 of the shaft 426.

As best shown in FIGS. 21G and 22A, the two housing components 212A, 212B have structures defined on their interior walls that are configured to mate with the various components contained within the housing 212, including the gears 420, 422 and bearings 430, 432. As such, the bearings 430, 432 are configured to be positioned within the appropriate mating features in the housing components 212A, 212B. These features secure the bearings 430, 432 in their intended positions in the housing 212 when the two housing components 212A, 212B are coupled. In addition, the rotation motor 416 is secured in its position within the housing 412 through a combination of the coupling or mating of the motor 416 with the features defined on the interior walls of the housing components 212A, 212B and two bolts or other type of threaded members 440A, 440B (one bolt—440A—is depicted) that are threaded through the holes 442A, 442B and into holes 444A, 444B defined in the motor 416.

In the depicted embodiment, the attachment component 424 is an attachment nut 424. However, it is understood that the specific geometry or configuration of the attachment component 424 can vary depending on the specific robotic device and the specific elbow joint configuration.

In use, the actuation of the rotation motor 416 actuates rotation of the attachment component 424, which results in rotation of the forearm 410, thereby rotating the end effector 414. As such, in one embodiment, the rotation of the end effector 414 is accomplished by rotating the entire forearm 410, rather than just the end effector 414. In the depicted embodiment, the forearm 410 rotates around the same axis as the axis of the end effector 414, such that rotation of the forearm 410 results in the end effector 414 rotating around its axis. Alternatively, the two axes can be offset.

Any known end effector can be coupled to the forearm 410. In this particular embodiment as shown in FIG. 21E, the end effector is a grasper 414 having a yoke 414.2 that is positioned around the proximal ends of the grasper components 414.1. In this embodiment, the grasper 414 has a configuration and method of operation substantially similar to the grasper disclosed in U.S. application Ser. No. 13/493, 725, filed on Jun. 11, 2012, which is hereby incorporated herein by reference in its entirety. Alternatively, any known grasper configuration can be used.

Figure 23A:
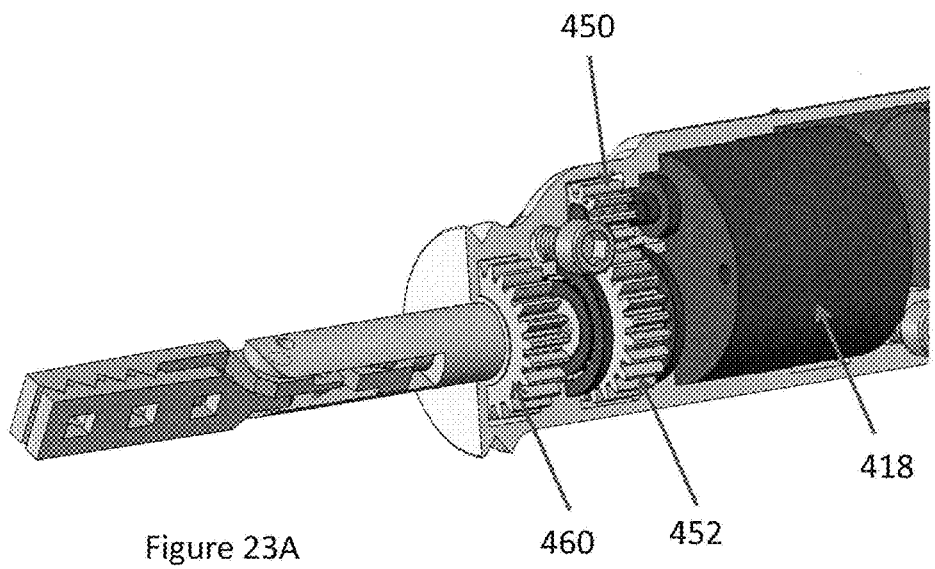
FIG. 23A is a cutaway close-up view of the grasper end of the forearm and internal components of a robotic device, according to another embodiment.
Figure 23B:
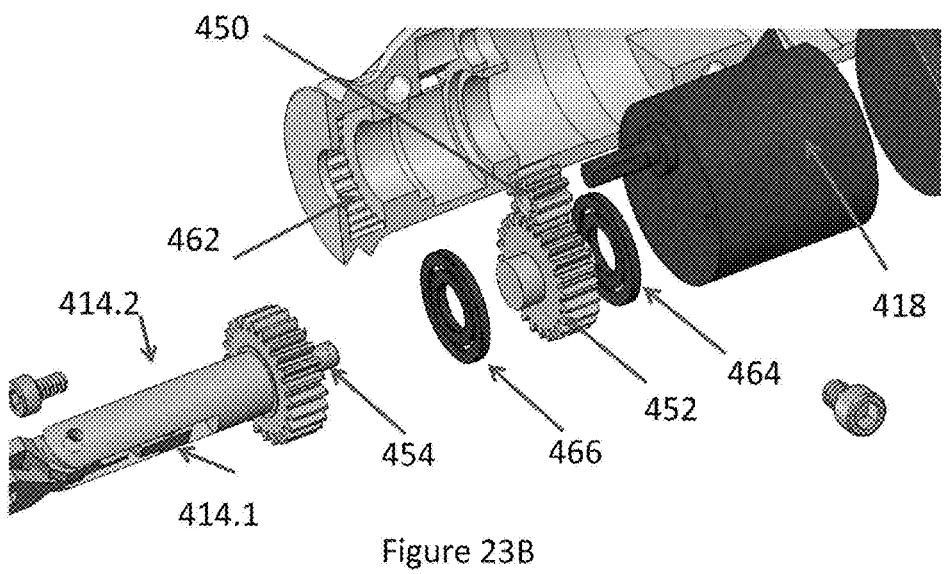
FIG. 23B is an exploded close-up view of the grasper end of the forearm and internal components of a robotic device, according to the embodiment of FIG. 23A.

As best shown in FIGS. 21E, 23A, and 23B, the end effector motor 418 is configured to actuate the grasper 414 arms to open and close via the motor gear 450, which is coupled to the coupling gear 452, which is coupled to center drive rod 454, which is coupled to the grasper components 414.1. The grasper yoke 414.2 is substantially fixed to the housing 412 so that it does not move relative to the housing 412. More specifically, the grasper yoke 414.2 is fixedly coupled to the yoke gear 460, which is positioned in the housing 412 such that it is mated with the ridged notch 462 defined in the inner wall of the housing 412, as best shown in FIG. 23B. The teeth of the yoke gear 460 mate with the ridges of the ridge notch 462 to thereby couple the gear 460 and the housing 412. In addition, according to certain embodiments, glue can be placed between the yoke gear 460 and the housing as well, to further enhance the fixation of the grasper yoke 414.2 to the housing 412.

The coupler gear 452 has a center hole (not shown) that is internally threaded (not shown) such that the proximal end of the center drive rod 454 is positioned in the center hole. Because the center drive rod 454 has external threads (not shown) that mate with the internal threads of the center hole defined in the coupler gear 452, the rotation of the coupler gear 452 causes the internal threads of the center hole to engage the external threads of the drive rod 454 such that the drive rod 454 is moved translationally. This translational movement of the drive rod 454 actuates the grasper arms to move between the closed and open positions. The coupler gear 452 is supported by two bearings 464, 466, which are secured within the housing 412 by appropriate features defined in the inner walls of the housing 412. In addition, the end effector motor 418 is secured in a fashion similar to the motor 416.

In an alternative embodiment, the grasper or other end effector can be actuated by any known configuration of actuation and/or drive train components.

In one implementation, when the forearm 410 and the end effector 414 are assembled, the forearm 410 can have a gap 470 between the two motors 416, 418. In accordance with one embodiment, the gap 470 can be a wiring gap 470 configured to provide space for the necessary wires and/or cables and any other connection components needed or desired to be positioned in the forearm 410.

Figure 24:
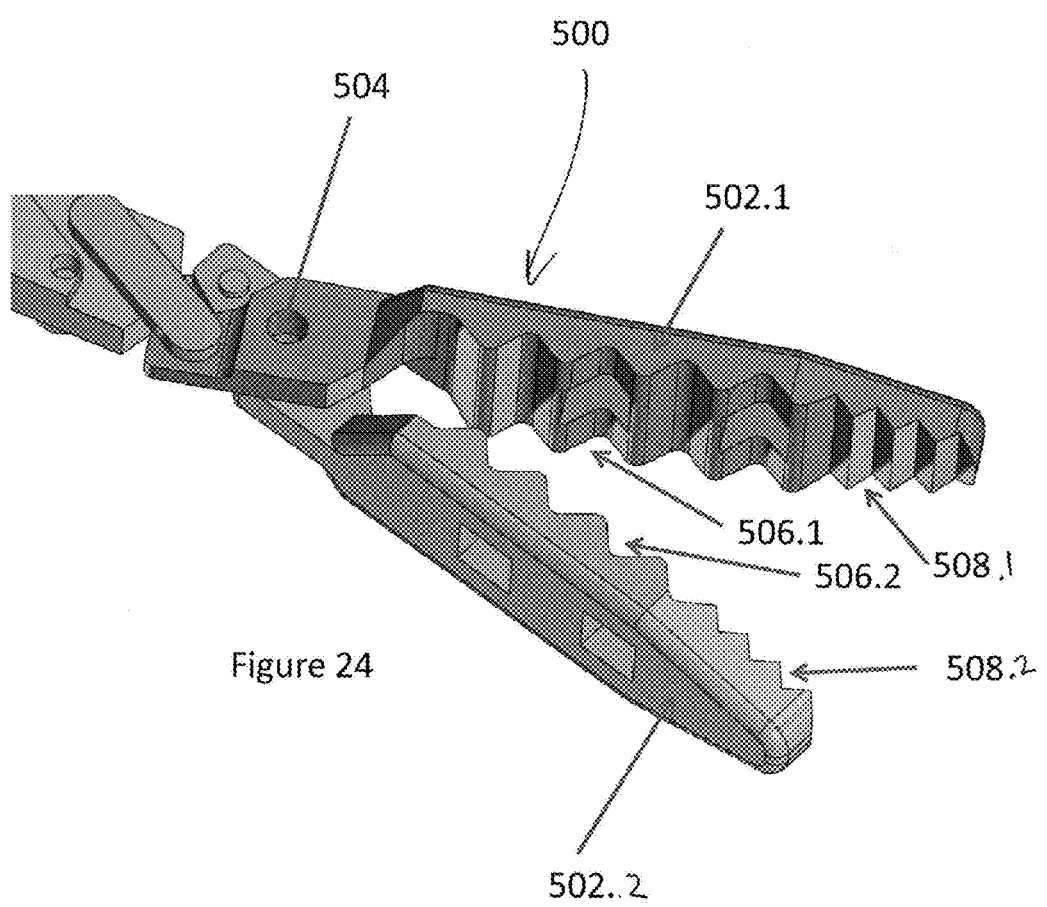
FIG. 24 is a perspective close-up view of the grasper of a robotic device, according to another yet implementation.

As discussed above, any end effector can be used with the robotic device embodiments disclosed and contemplated herein. One exemplary implementation of a grasper 500 that can be used with those embodiments is depicted in FIG. 24. The grasper 500 has two jaws (also referred to as arms) 502.1, 502.2 that both pivot around a single pivot point 504. According to one embodiment, the grasper 500 is a "combination" or "hybrid" grasper 500 having structures configured to perform at least two tasks, thereby reducing the need to use one tool for one task and then replace it with another tool for another task. More specifically, each jaw 502.1, 502.2 has two sizes of ridges or toothlike formations ("teeth"): larger teeth 506.1, 506.2 and smaller teeth 508.1, 508.2. It is understood that the teeth can be any known size for use in grasper jaws, so long as one set (the larger set) is larger than the other set (the smaller set). The larger teeth 506.1, 506.2 are intended for gross manipulations (dealing with larger amounts of tissue or larger bodies in the patient) while the smaller teeth 508.1, 508.2 are intended for finer work (such as manipulating thin tissue). In use, when fine work is to be performed, only the distal ends or tips of the jaws 502.1, 502.2 are used such that only the smaller teeth 508.1, 508.2 are used.

In one embodiment, the portion of the jaws 502, 502.2 having the smaller teeth 508.1, 508.2 is narrower in comparison to the portion having the larger teeth 506.1, 506.2, thereby providing a thinner point that can provide more precise control of the grasper 500.

Figure 25A:
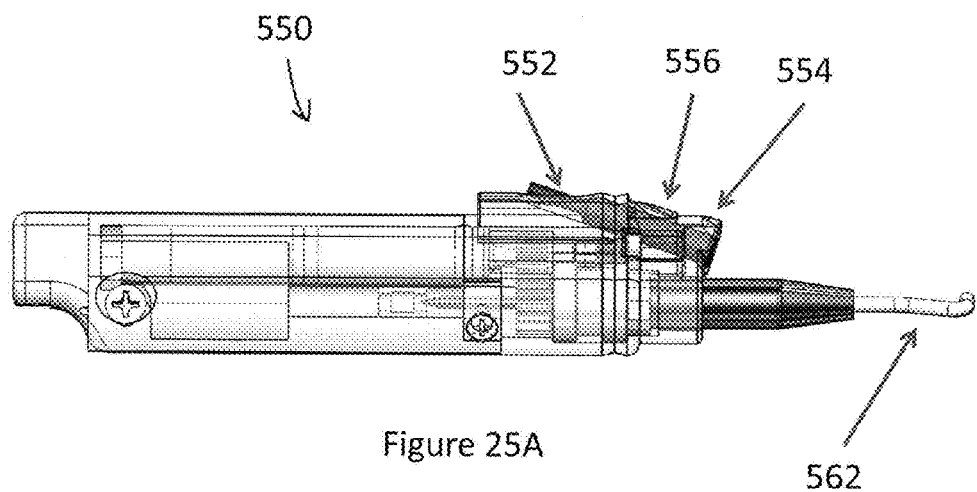
FIG. 25A is a see-through side view of the forearm having a camera and internal components of a robotic device, according to another embodiment of the system.
Figure 25B:
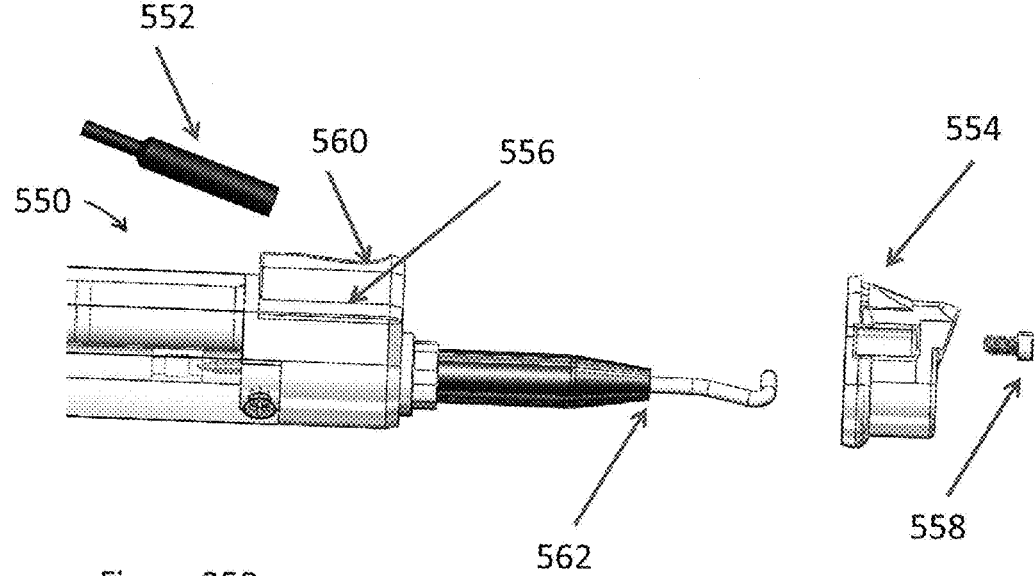
FIG. 25B is an exploded and see-through view of the forearm having a camera of a robotic device, according to the embodiment of FIG. 25A.
Figure 25C:
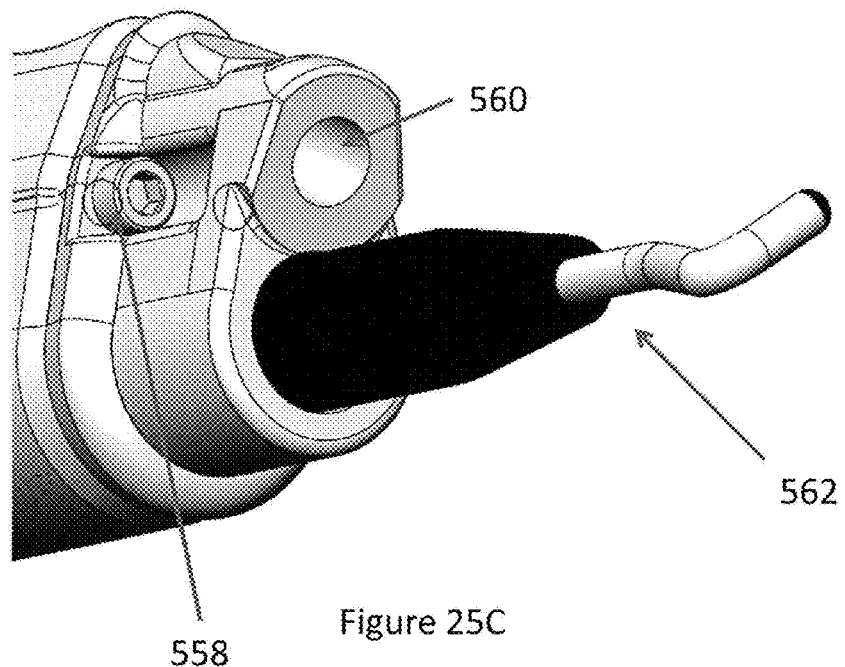
FIG. 25C is a close up perspective view of the forearm having a camera of a robotic device, according to the embodiment of FIG. 25A.
Figure 25D:
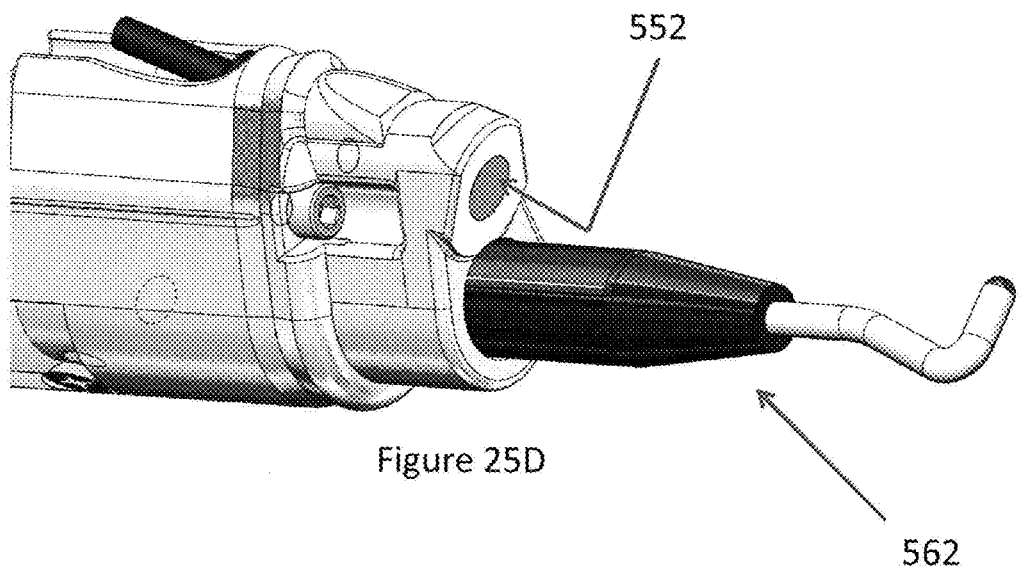
FIG. 25D is another close up perspective view of the forearm having a camera of a robotic device, according to the embodiment of FIG. 25A.

In accordance with one implementation, a robotic device according to any of the embodiments disclosed herein can also have at least one forearm 550 with a camera 552 as shown in FIGS. 25A-25E. As best shown in FIGS. 25A, 25B, and 25C, one embodiment of the forearm 550 with a camera 552 has a lumen 560A defined through a camera housing 556 positioned at the distal end of the forearm 550. In addition, the forearm 550 also has an end cap 554 that defines a portion of the lumen 560B as well, as best shown in FIG. 25C. When the end cap 554 is positioned on the distal end of the forearm 550, the lumens 560A, 560B are coupled to produce a single lumen 560. In one embodiment, the end cap 554 is coupled to the distal end of the forearm 550 by sliding the cap 554 over the end effector 562 (which, in this particular embodiment, is a cautery component 562) and secured to the distal end of the forearm 550 using at least one screw 558. The camera 552 can be positioned within the lumen 560 as best shown in FIGS. 25A and 25D.

Figure 25E:
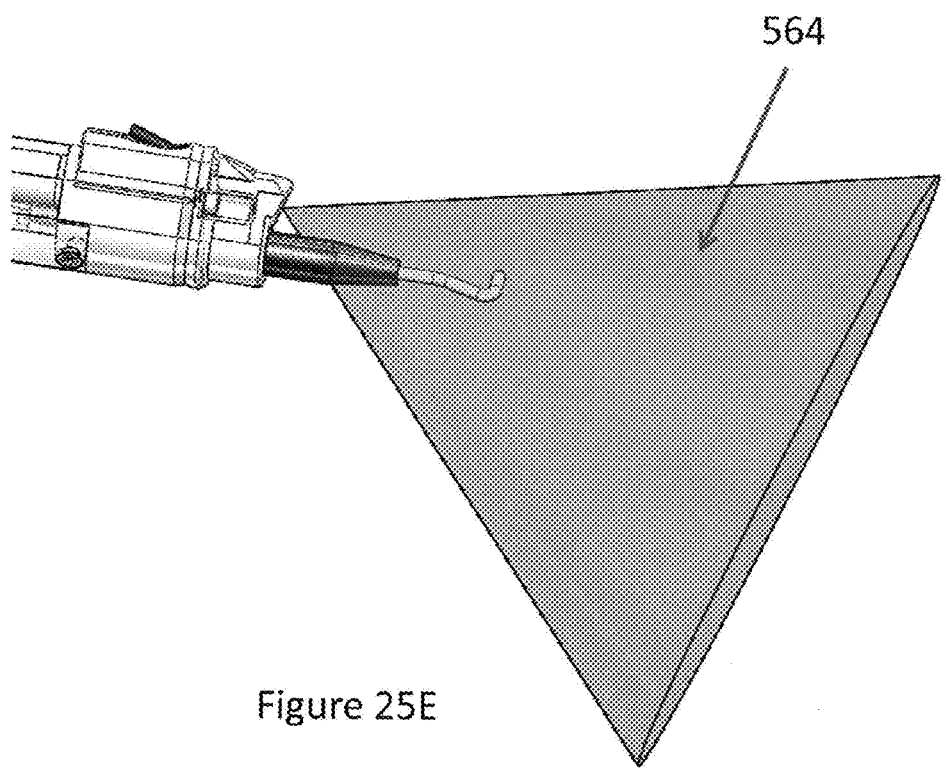
FIG. 25E is a perspective view of the forearm having a camera detailing the camera's field of vision for a robotic device, according to the embodiment of FIG. 25A.

In use, the camera 552 provides a secondary viewpoint of the surgical site (in addition to the main camera on the robotic device (such as, for example, the camera 99 described above) and could potentially prevent trauma by showing a close-up view of the site. In one embodiment, the camera 552 is positioned such that the field of view contains the tip of the cautery (or any other end effector) 562 and as much of the surgical site as possible. One embodiment of the field of view 564 provided by the camera 552 is depicted in FIG. 25E, in which the field of view cone is 60 degrees. Alternatively, the field of view can be any known size for a camera that can be incorporated into a medical device. In a further alternative, multiple cameras could be incorporated into the distal end of the forearm 550. In one embodiment, multiple cameras could be configured to provide stereoscopic ("3D") visualization. In a further alternative implementation, the distal end of the forearm 550 could also have lights such as, for example, LED or fiber optic lights for illumination. While this particular embodiment depicts the camera 552 being used on a cautery forearm 550, the camera 552 or any similar variation of the camera 552 as contemplated herein can be incorporated into any robotic end effector in which an alternate view would be beneficial. According to further alternative implementations, the camera unit could be positioned in a location on a robotic device other than the forearm. In accordance with one embodiment, the one or more additional viewpoints provided by one or more additional cameras can be shown as a Picture In Picture (PIP) on the surgical user interface or on separate monitors.

In use, the various embodiments of the robotic device disclosed and contemplated herein can be positioned in or inserted into a cavity of a patient. In certain implementations, the insertion method is the method depicted in FIGS. 26A-26F. In this method, the entire device 602 can be inserted into the cavity as a single device, in contrast to those prior art devices that must be inserted in some unassembled state and then assembled after insertion. That is, many known surgical robotic devices prior to the embodiments disclosed herein require a relatively extensive process for insertion into the abdominal cavity. For such prior art devices, each arm must be inserted individually, aligned with a central connecting rod that is also inserted, and then coupled to the connecting rod to secure the arms in place. Other similar procedures require some similar set of steps relating to the insertion of various separate parts of a device, followed by some assembly of the parts once they are positioned as desired in relation to the patient. These insertion-then-assembly procedures are generally time-consuming procedures that expose the robotic arms to fluids within the cavity for the duration of the process. As such, these procedures can often lead to premature failure of the robots due to moisture damage of the electronics and undue stress on the arms during assembly.

Figure 26A:
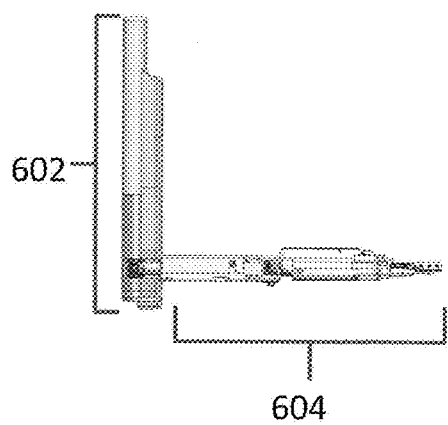
FIG. 26A is a side view of the forearm and body of a robotic device in one position, according to another embodiment.
Figure 26B:
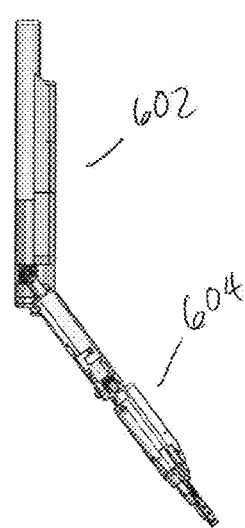
FIG. 26B is a side view of the forearm and body of a robotic device in one position, according to the embodiment of FIG. 26A.
Figure 26C:
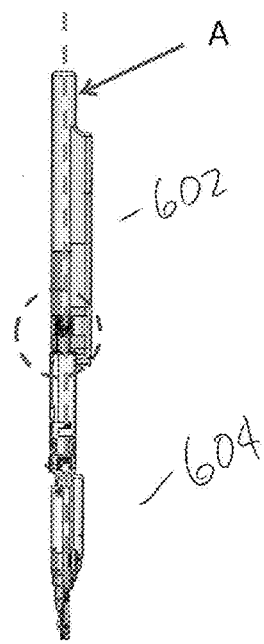
FIG. 26C is a side view of the forearm and body of a robotic device in one position, according to the embodiment of FIG. 26A.

In contrast, the device embodiments disclosed herein allow for inserting the entire device without any post-insertion assembly, thereby eliminating the problems described above. More specifically, the shoulder joint configuration and the reduced profile created by that configuration allows the entire device to be inserted as a single unit with both arms intact. FIGS. 26A-26F depict the various positions of the device arms 604 during the insertion procedure, according to one embodiment. FIG. 26A depicts the base or homing position required by the control kinematics. That is, as is understood by those of ordinary skill in the art, robotic devices typically have encoders that track the current position of the moving parts of the device (such as, for example, the arms 604 on this device), but the encoders track the relative position, not the actual position. As such, the homing position is necessary in order for the device to start from a known configuration. FIG. 26B depicts the arms 604 in a transition position in which the arms 604 are moving from the homing position toward the fully extended vertical position of FIG. 26C. The shoulders are then re-positioned to the configuration shown in FIG. 26D (and in further detail in FIG. 27A in which the insertion tube 600 is depicted) in which the arms 604 are rotated to a position in which they are no longer positioned along the same vertical axis (X1) as the device body 602, but instead are positioned such that the axis (X2) of the arms 604 is parallel to and behind the device body 602. In addition, the rotation of the arms 604 to the position of 26D (and 27A) also results in the cross-sectional profile of the device 602 along its width being reduced by the size of the arms 604. That is, while the arms 604 in 26C are positioned alongside the device body 602 such that the width of the body 602 is enlarged by the width of the arms 604 on each side of the body 602, the rotation of the arms 604 to a position behind the body 602 also results in the arms 604 being positioned such that they are positioned within the width of the body 602 (that is, they do not extend beyond the width of the body 602). It is the configuration of the shoulders as described above that allows for this particular repositioning. The end result is a device configuration in 26D that has a smaller width than the configuration in 26C, thereby reducing the profile of the device along its width and allowing for insertion of the device without having to remove the arms.

Figure 26D:
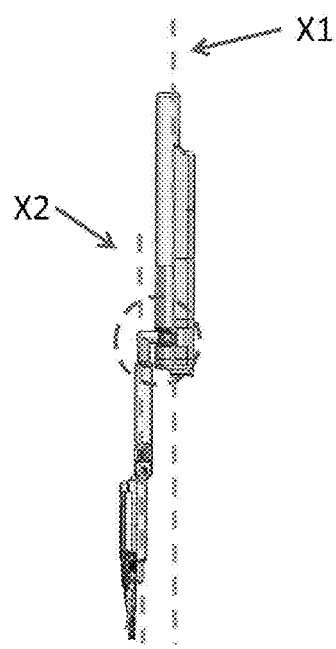
FIG. 26D is a side view of the forearm and body of a robotic device in one position, according to the embodiment of FIG. 26A.
Figure 26E:
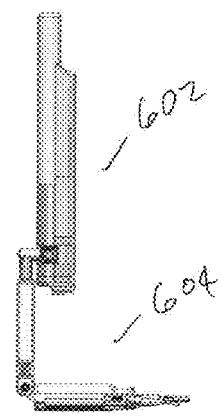
FIG. 26E is a side view of the forearm and body of a robotic device in one position, according to the embodiment of FIG. 26A.
Figure 26F:
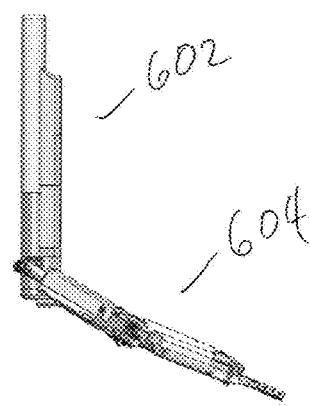
FIG. 26F is a side view of the forearm and body of a robotic device in one position, according to the embodiment of FIG. 26A.

Once the device is in the configuration of FIG. 26D, the device can begin to be inserted into the cavity. Due to the length of the arms, the device cannot be fully inserted into the cavity in this vertical position, so once the forearms are positioned inside the cavity, they are rotated to the position shown in FIG. 26E (and in further detail in FIG. 27B). Once in this configuration, the rest of the robot is fully inserted and then the device is configured into a typical operating arrangement such as that shown in FIG. 26F (and in further detail in FIG. 27C).

Figures 27A, 27B, 27C:
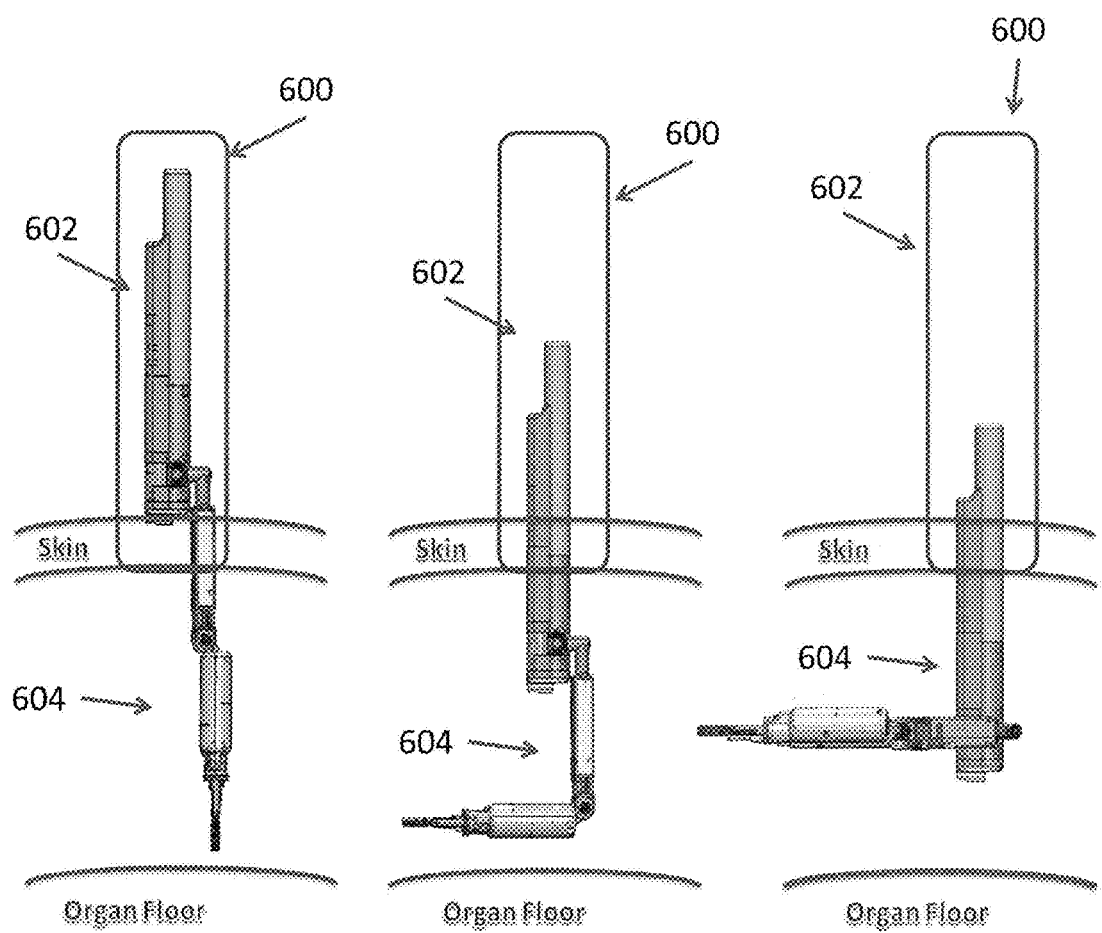
FIG. 27A is a side view of the forearm and body of a robotic device in one position inside the body, according to another embodiment.
FIG. 27B is a side view of the forearm and body of a robotic device in one position inside the body according to the embodiment of FIG. 27A.
FIG. 27C is a side view of the forearm and body of a robotic device in one position inside the body, according to the embodiment of FIG. 27A.

The alternative embodiment depicted in FIGS. 27A-27C depict an insertion tube (also called an "overtube") 600 in which the robotic device can be stored prior to use. Further, prior to insertion, the tube 600 will be sealed to the abdominal wall after an incision has been made in the wall. Once sealed, the abdomen can be insufflated between the skin 1000 and organ floor 1002 and the blue overtube and abdomen will be at equal pressures. The robot can then be inserted following the previously outlined steps discussed above.

Figure 28:
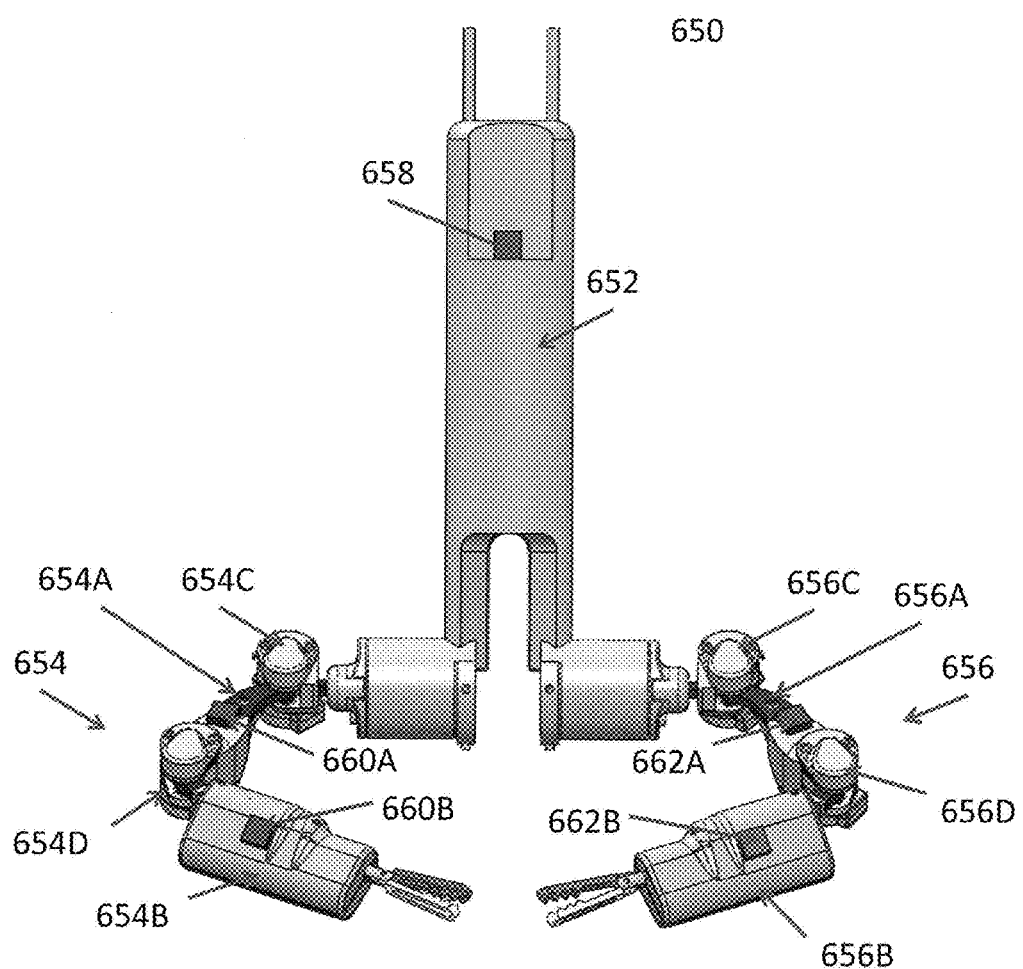
FIG. 28 is front view of a robotic device, according to one embodiment.

According to another embodiment, any of the robotic devices disclosed or contemplated above can also incorporate sensors to assist in determining the absolute position of the device components. As depicted in FIG. 28, the robotic device 650 has a body 652, a right arm 654, and a left arm 656. The right arm 654 has an upper arm 654A and a forearm 654B, and the left arm 656 also has an upper arm 656A and a forearm 656B. Note that each of the upper arms and forearms are also referred to as "links." In addition, the right arm 654 has a shoulder joint 654C and an elbow joint 654D, while the left arm 656 also has a shoulder joint 656C and an elbow joint 656D.

In this embodiment, various position sensors 658, 660A, 660B, 662A, 662B are positioned on the device 650 as shown in FIG. 28. More specifically, a first position sensor 658 is positioned on the device body 652, while a second position sensor 660A is positioned on the right upper arm 654A, a third position sensor 660B is positioned on the right forearm 654B, a fourth position sensor 662A is positioned on the left upper arm 656A, and a fifth position sensor 662B is positioned on the left forearm 656B. In accordance with one implementation, the sensors are 3-axis sensors, as described in FIG. 29. In one embodiment, the position sensor 658 positioned on the device body 652 senses the orientation of the device body 652 and then the orientation of each of the sensors 660A, 660B, 662A, 662B on the links 654A, 654B, 656A, 656B can be used to determine the current position of each link of each arm 654, 656 and the joint angles at joints 654C, 654D, 656C, 656D.

More specifically, the sensor 658 positioned on the device body 652 is used as the known reference point, and each of the other sensors 660A, 660B, 662A, 662B can be used in conjunction with the sensor 658 to determine the position and orientation of both arms relative to the reference point. In one implementation, each 3-axis sensor measures the spatial effect of the at least one environmental characteristic being measured and also determine the orientation of that sensor in all three spatial dimensions. Each sensor 660A, 660B, 662A, 662B on a link 654A, 654B, 656A, 656B measures the environmental characteristic at that position on the link. For each link 654A, 654B, 656A, 656B, the measured value and orientation of the sensor 660A, 660B, 662A, 662B on that link can then be used to determine the spatial orientation of each link 654A, 654B, 656A, 656B. When sensors are mounted on every link as in FIG. 28, the kinematic configuration of both robotic arms 654, 656 can be used with the link orientations determined from the sensors to directly calculate the position of the arms 654, 656 from the known reference point: sensor 658. This known orientation can then be used to determine the position and orientation of both arms 654, 656 relative to the reference point 658.

While the sensors 660A, 660B, 662A, 662B in FIG. 28 are shown to be attached to an exterior surface of each link as shown, in alternative embodiments the sensors can be mounted on the link in any known or measureable position and orientation. In a further alternative, each of the sensors can be mounted in an interior location inside the particular component that the sensor is intended to be coupled to. In yet another alternative, each sensor can be positioned on an exterior portion of the appropriate component as long as it is firmly attached to the component.

In addition, it is understood that while the embodiment in FIG. 28 depicts a robotic device 650 with two joints and two links per arm, the position sensors can be applied to and used with a robotic device with any number of joints and links per arm in any configuration.

Figure 29:
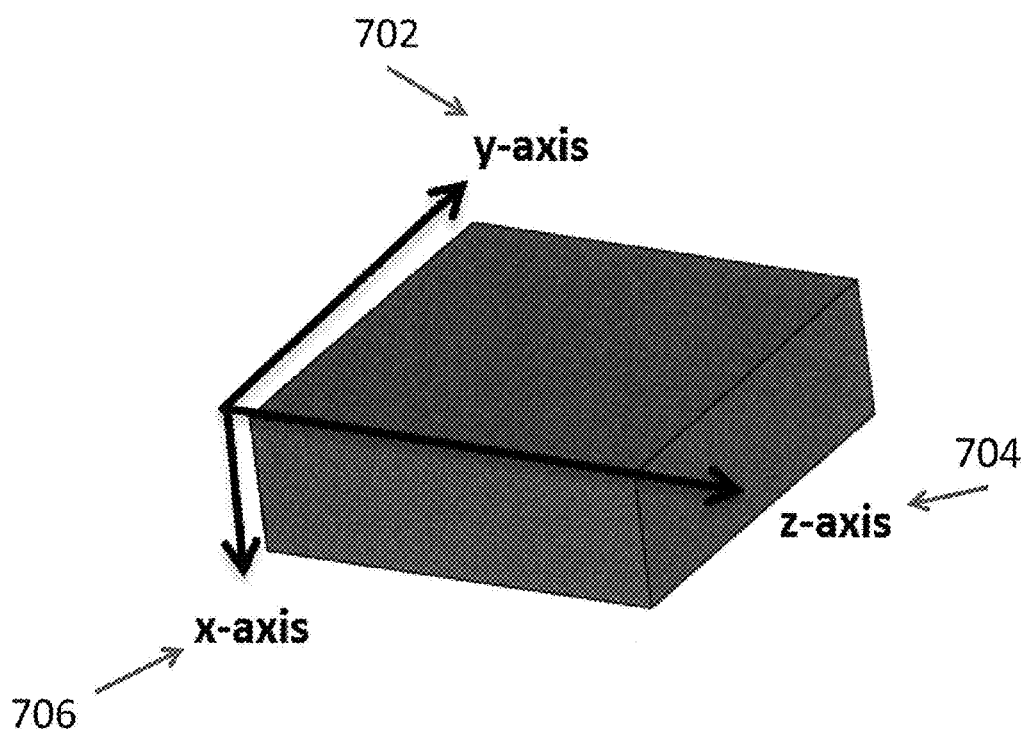
FIG. 29 is a perspective view of an accelerometer according to one embodiment, showing the axis of detection.

In one embodiment, the 3-axis sensors 658, 660A, 660B, 662A, 662B are 3-axis accelerometers that measure the acceleration due to gravity. It is understood that a 3-axis accelerometer operates in the following fashion: the acceleration due to gravity is measured and depending on the orientation of the arm link (or other device component), magnitudes of acceleration in proportion to the orientation angles of the accelerometer are sensed on the different axes 702, 704, 706 of the 3-axis accelerometer as best shown in FIG. 29. Given the acceleration measurements on each axis of the accelerometer, the orientation of the link that the accelerometer is mounted on can be determined with respect to gravity.

Aside from being able to measure the acceleration of gravity, one additional characteristic of accelerometer sensors is that they can also measure the acceleration of the link(s) they are attached to on the robotic device. As such, in certain embodiments, given a starting position for the robotic device and its links, this acceleration data can be integrated over time to provide a position for the links of the robot. The positions determined from this integration can be more accurate if the system model of the robot is known to help account for the effects of inertia and other internal forces.

Alternatively, sensors other than accelerometers can be used. Possible sensors include, but are not limited to, magnetometers (measuring magnetic field from earth's magnetic field, induced magnetic field, or other magnetic field), tilt sensors, radio frequency signal strength meters, capacitance meter, or any combination or extensions of these. Further, while 3-axis sensors are used in the embodiment discussed above, single or dual or other multi-axis sensors could be used.

Another type of sensor that can be used with a robotic device is a gyroscope. The gyroscope measures the rate of rotation in space. The gyroscope can be combined with an accelerometer and magnetometer to form an inertial measurement unit, or IMU, that can be used to measure the static position of the robotic device or to calculate the position of the device while it is moving through integration of the measured data over time.

In use, the sensors described above help to determine or provide information about the absolute position of a device component, such as an arm. This contrasts with many known robotic devices that use embedded encoders, which can only measure a relative change in a joint angle of an arm such that there is no way to determine what position the arm is in when the device is first powered up (or "turned on"). The sensor system embodiments described herein help to determine the absolute position of one or more links on a robotic device. In fact, in accordance with some implementations, the position tracking systems disclosed herein allow a robotic device or a user to autonomously determine what position the device and device arms are in at any time. Such a system according to the embodiments disclosed herein can be used alone (as a primary position tracking system) or in combination with the embedded encoders (as a redundant position tracking system). Although as previously described only one position sensor is used per link, other embodiments have multiple sensors per link. The additional position sensors provide additional positional redundancy, and in some implementations the data collected from the multiple position sensors can be used with various filtering techniques, such as Kalman Filtering, to provide a more robust calculation of the position of the robot.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the present invention has been described with reference to preferred embodiments, persons skilled in the art will recognize that changes may be made in form and detail without departing from the spirit and scope of the invention.

We claim:

1. A surgical robotic system, comprising:
   a. an insertion tube adapted for traversing the body of a patient into a body cavity;
   b. a robotic device configured to be completely disposed within the body cavity, comprising:
      i. an elongate device body comprising:
         A. first and second ends defining a longitudinal axis;
         B. at least one housing;
         C. a plurality of motors disposed within the at least one housing; and
         D. a first shoulder joint and a second shoulder joint, wherein the first and second shoulder joints are operably coupled to the plurality of motors;
         wherein the elongate body defines a horizontal plane through the first and second shoulder joints and the longitudinal axis; and
         further wherein the elongate body is configured so as to be capable of traversing the insertion tube from the exterior to interior of the patient;
      ii. a first movable segmented robotic arm operationally connected to the first shoulder joint, wherein the first moveable segmented robotic arm comprises a first link and second link joined by an elbow joint;
      iii. a second movable segmented robotic arm operationally connected to the second shoulder joint, wherein the second moveable segmented robotic arm comprises a first link and second link joined by an elbow joint;
      iv. a first operational component operationally connected to the first robotic arm; and
      v. a second operational component operationally connected to the second robotic arm; and
   c. an operations system for control of the robotic device from outside the patient by way of the insertion tube and device body, the operations system in electrical communication with the robotic device,
   wherein the first and second segmented robotic arms are configured to be positioned in at least:
      i. a first fully extended position coplanar with the horizontal plane defined by the body and the first and second shoulder joints and coaxial with the longitudinal axis; and
      ii. a second offset position, non-coplanar with the horizontal plane defined by the body and shoulders, wherein the segmented robotic arms are substantially parallel with the longitudinal axis.

2. The surgical robotic system of claim 1, wherein the first and second shoulder joints are operationally coupled to device body motors so as to be capable of inducing yaw and pitch.

3. The surgical robotic system of claim 2, wherein the first and second segmented arm elbow joints are operationally configured to be capable of yaw.

4. The surgical robotic system of claim 3, further comprising a plurality of position sensors.

5. The surgical robotic system of claim 4, wherein the at least one position sensor is a 3-axis sensor.

6. The surgical robotic system of claim 4, wherein first and second operational components are end effectors operationally connected to the segmented arm.

7. The surgical robotic system of claim 6, wherein at least one of the end effectors is selected from a group consisting of a grasping component, a cauterizing component, a suturing component, an imaging component, an irrigation component, a suction component, an operational arm component, a sensor component, and a lighting component.

8. The surgical robotic system of claim 4, wherein at least one of the end effectors is in operational communication with the operations system so as to be actuated by a user located outside the body of the patient.

9. The surgical robotic system of claim 2, wherein the device body motors further comprise a plurality of proximal motors operationally coupled with the first and second shoulder joints to actuate shoulder yaw and a plurality of distal motors operationally coupled with the first and second shoulder joints to actuate shoulder pitch.

10. The surgical robotic system of claim 3, wherein the first and second segmented robotic arms further comprise upper arm motors operationally coupled with the first and second elbow joints to actuate elbow yaw.

11. The surgical robotic system of claim 10, further comprising a plurality of bevel gears operationally coupled to the upper arm motors and elbow joints.

12. A surgical robotic system, comprising:
    a. a insertion tube;
    b. a robotic device comprising:
       i. an elongate body component defining at least one housing, first and second ends, and first and second sides, the device body comprising:
          A. at least one first side motor disposed within the at least one housing; and
          B. at least one second side motor disposed within the at least one housing,
          wherein the first end and second end define a longitudinal axis and a length between the first end and second end, and
          wherein the first side and second sides define a width;
       ii. a first shoulder joint adjacent and operably coupled to the at least one first side motor;
       iii. a second shoulder joint adjacent and operably coupled to the at least one second side motor;
       iv. a first movable segmented robotic arm operationally connected to the body component by way of the first shoulder joint and further comprising a first elbow joint;
       v. a second movable segmented robotic arm operationally connected to the body component by way of the second shoulder joint and further comprising a second elbow joint;
       vi. a first operational component operationally connected to the first movable segmented robotic arm; and
       vii. a second operational component operationally connected to the second movable segmented robotic arm; and
    c. an operations system for control of the robotic device from outside the patient by way of the insertion tube and body, the operations system in electrical communication with the robotic device, wherein the first and second segmented robotic arms are configured to be positionable in:
  i. a first fully extended position wherein the arms are coaxial with the longitudinal axis and coplanar with the body width; and
  ii. a second position wherein the arms are substantially parallel to the longitudinal axis and non-coplanar with the width.

13. The surgical robotic system of claim 12, wherein the robotic device comprises a plurality of motors configured to actuate the segmented robotic arms.

14. The surgical robotic system of claim 13, wherein first shoulder joint is configured to be capable of driving yaw and pitch rotation of the first movable segmented robotic arm relative to the elongate body and the second shoulder joint is configured to be capable of driving yaw and pitch rotation of the second movable segmented robotic arm relative to the elongate body.

15. The surgical robotic system of claim 14, wherein the first and second segmented arm elbow joints are configured to be capable of yaw.

16. The surgical robotic system of claim 15, wherein the first and second operational components are end effectors chosen from a group consisting of a grasping component, a cauterizing component, a suturing component, an imaging component, an irrigation component, a suction component, an operational arm component, a sensor component, and a lighting component.

17. A method of performing minimally invasive surgery, comprising:
  a. providing an insertion tube;
  b. providing a robotic device comprising:
    i. an elongate device body comprising at least one housing, first and second ends, and first and second sides and further comprising a plurality of motors disposed within the at least one housing, the device body being configured for traversing the insertion tube from the exterior to interior of the patient so as to be completely inserted within the patient,
    ii. a first shoulder joint in operable communication with the plurality of motors disposed within the housing and configured to be capable of yaw and pitch rotation;
    iii. a second shoulder joint in operable communication with the plurality of motors disposed within the housing and configured to be capable yaw and pitch rotation;
    iv. a first movable segmented robotic arm operationally connected to the first shoulder joint further comprising an elbow joint configured for yaw;
    v. a second movable segmented robotic arm operationally connected to the second shoulder joint further comprising an elbow joint configured for yaw;
    vi. a first operational component operationally connected to the first robotic arm; and
    vii. a second operational component operationally connected to the second robotic arm; and
  c. providing an operations system for control of the robotic device from outside the patient by way of the insertion tube and device body, the operations system in electrical communication with the robotic device,
wherein the ends and sides of the device body define a horizontal body plane, and further wherein the first and second segmented robotic arms are configured to be selectively positionable in at least:
  i. a first substantially parallel, fully extended position coplanar with the horizontal body plane; and
  ii. a second substantial parallel, non-coplanar position with the horizontal body plane.

18. The method of performing minimally invasive surgery of claim 17, wherein the first and second operational components are end effectors chosen from a group consisting of a grasping component, a cauterizing component, a suturing component, an imaging component, an irrigation component, a suction component, an operational arm component, a sensor component, and a lighting component.

19. The method of performing minimally invasive surgery of claim 18, further comprising adjusting and tracking the position of the end effectors by way of the operations system, robotic arms and at least one position sensor.

20. The method of performing minimally invasive surgery of claim 19, wherein the position sensor is a 3-axis sensor.

* * * * *